United States Patent [19]
Namikoshi et al.

[11] Patent Number: 5,368,737
[45] Date of Patent: Nov. 29, 1994

[54] SEPARATION AGENT COMPRISING ACYL-OR CARBAMOYL-SUBSTITUTED POLYSACCHARIDE

[75] Inventors: Hajime Namikoshi; Tohru Shibata; Ichiro Okamoto, all of Himeji, Japan

[73] Assignee: Daicel Chemical Industries, Ltd., Osaka, Japan

[21] Appl. No.: 156,256

[22] Filed: Nov. 22, 1993

Related U.S. Application Data

[60] Division of Ser. No. 51,482, Apr. 22, 1993, abandoned, which is a division of Ser. No. 889,042, May 26, 1992, Pat. No. 5,229,002, which is a division of Ser. No. 778,792, Oct. 16, 1991, Pat. No. 5,137,638, which is a division of Ser. No. 643,463, Jan. 18, 1991, Pat. No. 5,075,009, which is a division of Ser. No. 392,764, Aug. 11, 1989, Pat. No. 5,017,290, which is a division of Ser. No. 358,895, May 30, 1989, Pat. No. 4,966,694, which is a division of Ser. No. 246,449, Sep. 19, 1988, Pat. No. 4,879,038, which is a continuation-in-part of Ser. No. 716,791, Mar. 27, 1985, abandoned.

[30] Foreign Application Priority Data

Mar. 29, 1984 [JP] Japan ................. 59365

[51] Int. Cl.$^5$ ............................. B01D 15/08
[52] U.S. Cl. .................. 210/635; 210/656; 210/198.2; 210/502.1; 502/404
[58] Field of Search ........... 502/404; 210/635, 656, 210/198.2, 502.1

[56] References Cited

U.S. PATENT DOCUMENTS

| | | | |
|---|---|---|---|
| 3,416,993 | 12/1968 | Heusser | 502/404 |
| 3,597,350 | 8/1971 | Determan | 210/656 |
| 3,960,720 | 6/1976 | Porath | 210/635 |
| 4,016,149 | 4/1977 | Travis | 210/635 |
| 4,111,838 | 9/1978 | Schaeffer | 210/656 |
| 4,322,310 | 3/1982 | House | 210/635 |
| 4,330,440 | 5/1982 | Ayers | 210/635 |
| 4,335,226 | 6/1982 | Muller | 210/656 |
| 4,431,544 | 2/1984 | Atkinson | 210/656 |
| 4,431,546 | 2/1984 | Hughes | 210/656 |
| 4,512,898 | 4/1985 | Oi | 210/656 |
| 4,522,724 | 6/1985 | Ramsden | 210/635 |
| 4,565,877 | 1/1986 | Wada | 210/656 |
| 4,767,571 | 8/1988 | Suzuki | 502/401 |
| 4,879,038 | 11/1989 | Namikoshi | 210/656 |

OTHER PUBLICATIONS

The Merck Index, Eighth Edition, Merck & Co., 1968, p. 635.
Optical Resolution on Polymers by Yoshio Okamoto—a publication presented at the 49th Spring Annual Meeting of the Chemical Society of Japan, Mar. 10, 1984, pp. 1–4.

Primary Examiner—Ernest G. Therkorn
Attorney, Agent, or Firm—Flynn, Thiel, Boutell & Tanis

[57] ABSTRACT

Separation of a chemical substance is effected by treating a mixture thereof with a polysaccharide having a substituent for hydroxyl group an acyl group of the formula (1) or a carbamoyl group of the formula (2):

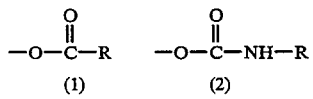

wherein R represents an atomic group having a nucleus comprising a conjugated $\pi$-bond system in which the number of bonds interposed between an atom contained therein and bonded with the carbonyl or amino group and an atom contained in the $\pi$-bond system and most distant from said atom is at least 5 even in the shortest route.

9 Claims, 1 Drawing Sheet

SEPARATION AGENT COMPRISING ACYL-OR CARBAMOYL-SUBSTITUTED POLYSACCHARIDE

This is a division of Ser. No. 08/051,482, filed Apr. 22, 1993, now abandoned which is a division of Ser. No. 07/889,042, filed May 26, 1992, now U.S. Pat. No. 5,229,003 which is a division of Ser. No. 07/778,792, filed Oct. 16, 1991, now U.S. Pat. No. 5,137,638, which is a division of Ser. No. 07/643,463, filed Jan. 18, 1990, now U.S. Pat. No. 5,075,009, which is a division of Ser. No. 07/392,764, filed Aug. 11, 1989, now U.S. Pat. No. 5,017,290, which is a division of Ser. No. 07/358,895, filed May 30, 1989, now U.S. Pat. No. 4,966,694, which is a division of Ser. No. 07/246,449, filed Sep. 19, 1988, now U.S. Pat. No. 4,879,038, which is a continuation-in-part of Ser. No. 06/716,791, filed Mar. 27, 1985, now abandoned.

The invention relates to a separation agent which comprises a polysaccharide derivative having an acyl or a carbamoyl group as a substituent for a hydroxyl group. It has a conjugated π-bond system. The separation agent of the invention is useful for separation of various chemical substances, especially optical resolution of optical isomers. In addition, it serves for separation of geometrical isomers and polymers having different molecular weight ranges from each other. They have not easily been separated in the state of the prior art.

The resolving agent of the present invention can be used for separation of all sorts of chemical substances, particularly for optical resolution of them.

It has been well known that optical isomers of a chemical compound have effects different from each other in vivo generally. Therefore, it is an important problem to obtain chemically pure compounds for the purposes of improving medicinal effects per unit dose of the compounds or removing adverse reactions thereof and damage from them in medical, agricultural and biochemical fields. A mixture of optical isomers has been optically resolved by preferential crystallization process or diastereomer process. However, varieties of the compounds capable of being optically resolved by these processes are limited and these processes require a long time and much labor. Under these circumstances, development of a technique of conducting the optical resolution by an easy chromatographic process has eagerly been demanded.

Chromatographic optical resolution has been investigated from old times. However, resolving agents developed heretofore have problems that they have only an unsatisfactory resolution efficiency, compounds to be resolved should have a specific functional group or their stability is only poor. Thus, it has been difficult to optically resolve all sorts of compounds with satisfactory results.

An object of the present invention is to provide a resolving agent having a chemical structure different from those of known resolving agents and, therefore, resolving characteristics different from those of the known ones or a higher faculty of discriminating and identifying the optical isomers.

Particularly, the asymmetric structure of the polysaccharide is amplified by modifying it with a substituent having a sufficient length so as to obtain a higher faculty of identifying optical isomers.

The above-mentioned object of the present invention is attained by an agent for separation which contains as an effective component a polysaccharide derivative having as a substituent an acyl group of the following formula (1) or a carbamoyl group of the following formula (2):

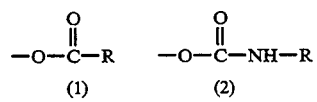

wherein R represents an atomic group having a nucleus comprising a conjugated π-bond system in which the number of bonds interposed between an atom contained therein and bonded with the carbonyl or amino group and an atom contained in the π-bond system and most distant from said atom is at least 5 even in the shortest route.

The resolving agent of the invention exhibits preferably different powers of adsorbing different optical isomers of a given compound.

In the identification of the asymmetric structure of a cellulose derivative such as cellulose tribenzoate or cellulose trisphenylcarbamate, an asymmetric space formed by adjacent substituents on $C_2$ and $C_3$ of the cellulose may contribute most greatly to the identification. Therefore, the inventors thought that the enlargement of said space would increase the faculty of identifying optical isomers. After intensive investigations, the inventors have found surprisingly that the polysaccharide derivatives having the above-mentioned substituents have quite excellent faculty of identifying optical isomers. The present invention has been completed on the basis of this finding.

The term "polysaccharide" herein involves any optically active polysaccharide selected from the group consisting of synthetic, natural and modified natural polysaccharides. Among them, those having highly regular bonds are preferred. Examples of them include β-1, 4-glucans (celluloses), α-1, 4-glucans (amylose and amylopectin), α-1, 6-glucan (dextran), β-1, 6 glucan (pustulan), β-1, 3-glucans (such as curdlan and schizophyllan), α-1, 3-glucan, β-1, 2-glucan (Crown gall polysaccharide), β-1, 4-galactan, β-1, 4-mannan, α-1, 6-mannan, β-1, 2-fructan (inulin), β-2, 6-fructan (levan), β-1, 4-xylan, β-1, 3-xylan, β-1, 4-chitosan, β-1, 4-N-acetylchitosan (chitin), pullulan, agarose and alginic acid. Still preferred ones are those capable of easily yielding highly pure polysaccharides, such as cellulose, amylose, β-1, 4-chitosan, chitin, β-1, 4-mannan, β-1, 4-xylan, inulin and curdlan.

These polysaccharides have a number-average degree of polymerization (average number of pyranose or furanose rings in the molecule) of at least 5, preferably at least 10. Though there is provided no upper limit of the degree of polymerization, it is preferably 500 or less from the viewpoint of easiness of the handling.

In the substituents of the polysaccharide derivatives of the following formulae according to the present invention:

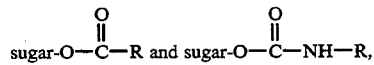

R represents an atomic group comprising a conjugated. π-bond system having at least a given length and capable of conjugation with the carbonyl or carboxyamino group. The term "at least a given length" herein means that the number of bonds interposed between an atom bonded with the carbonyl or carboxyamino group and an atom contained in the conjugated π-bond system and most distant from said atom is at least 5 in even the shortest route. The term "π-bond system" refers to not only usual double and triple bonds, but also lone electron pairs and vacant orbitals capable of conjugation with them. For example, in a p-methoxybenzoate group of the following formula:

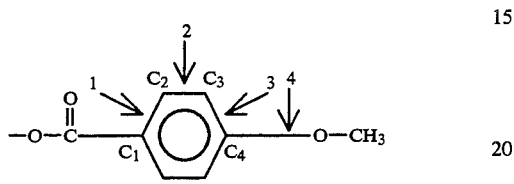

the conjugated π-bond system corresponding to R is conjugated with the carbonyl group. However, in this structure, the number of bonds interposed between an atom bonded with the carbonyl group, i.e., $C_1$, and an atom contained in the conjugated π-bond system and most distant from said atom ($C_1$), i.e., an oxygen atom of the methoxy group, is 4. Therefore, this structure is not included in the present invention. Examples of R included in the invention are as follows:

(1) substituted phenyl groups such as those shown below:

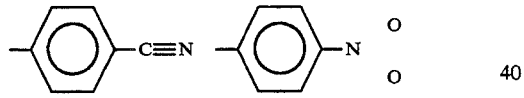

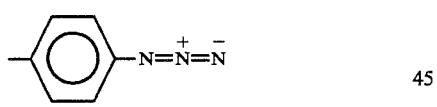

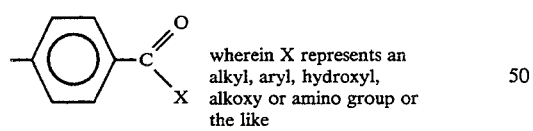 wherein X represents an alkyl, aryl, hydroxyl, alkoxy or amino group or the like

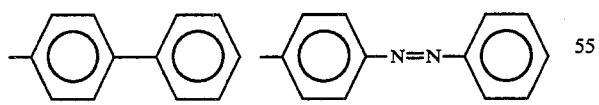

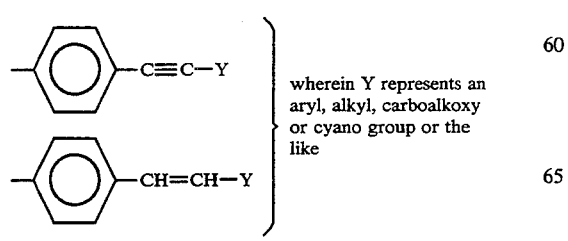 wherein Y represents an aryl, alkyl, carboalkoxy or cyano group or the like

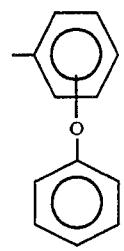

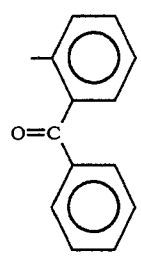

(2) phenylethenyl and phenylethynyl groups:

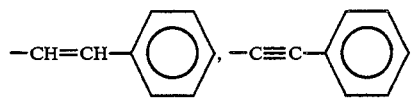

(3) condensed aromatic ring and condensed hetero aromatic ring groups such as those shown below:

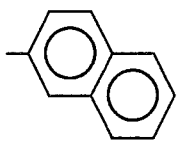

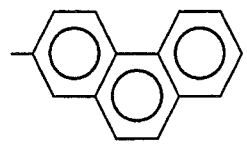

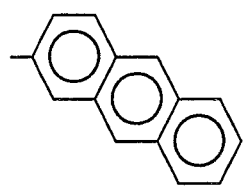

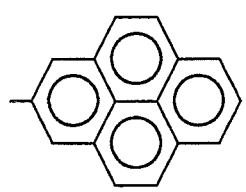

-continued

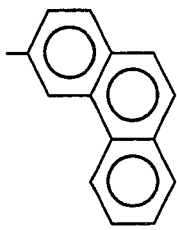

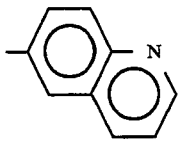

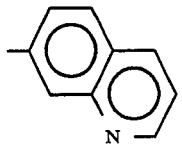

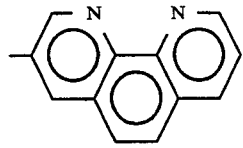

(4) condensed quinones such as those shown below:

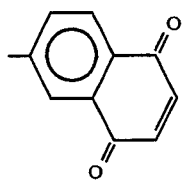

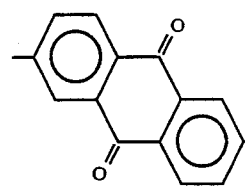

as well as substituted derivatives of them. The number, position and variety of the substituents are not particularly limited.

30 to 100%, preferably 85 to 100%, of the hydroxyl groups of the polysaccharides forming the derivatives should be acylated or carbamoylated in the present invention. The balance of the hydroxyl groups may be present in the form of free hydroxyl groups or they may be esterified, etherified or carbamoylated so far as the resolving capacity of the resolving agent is not damaged.

When a styryl or phenyl group is introduced into a cellulose or amylose triphenylcarbamate derivative, a high liquid-crystallizability or crystallizability is expectable, since the side chains are arranged regularly and the rigidity of the main chain is increased. Therefore, it was believed that these triphenyl derivatives might have an interesting optical resolution power.

Since an interesting change in the optical resolution power was observed when chloroform was added to the eluent, the effect of using chloroform with these polysaccharide derivatives was also investigated.

It also was believed that when

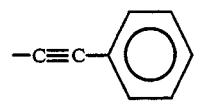

is introduced into position 4 of a cellulose triphenylcarbamate derivative, the conjugated system of the phenyl group would become larger and the characteristics of the side chain as the mesogenic group would become more remarkable. On the basis of this idea, cellulose tris[4-(2-phenylethynyl)phenylcarbamate] was examined with respect to its optical resolution power.

The optical resolution powers of triphenylcarbamates having an phenoxy group as a substituent also were investigated.

To synthesize the polysaccharide derivative used in the present invention, a corresponding polysaccharide is pretreated suitably, if necessary, and then reacted with an acylating agent or carbamoylating agent. The acylating agents include usually corresponding acid halides, acid anhydrides and mixed anhydrides with other strong acids. Usually, the reaction is conducted in the presence of a catalyst comprising a tertiary amine, particularly pyridine or an acidic substance. The carbamoylating agents include usually corresponding isocyanates. The reaction proceeds easily in the presence of a catalyst comprising a tertiary amine or a Lewis acid. In producing mixed derivatives, the substituted polysaccharide is reacted with these reagents or, alternatively, the polysaccharide is reacted with these reagents and then with other esterifying, etherifying or carbamoylating agent (see, for example, "Dai-Yuki Kagaku", 'Tennen Kobunshi Kagaku I and II', published by Asakura Book Store, and R. L. Whistler "Methods in Carbohydrate Chemistry" III, IV and V, published by Academic Press).

The resolving agent of the present invention is used for the purpose of resolving compounds and optical isomers thereof generally according to a chromatographic method such as gas, liquid or thin layer chromatographic method. Further, the resolving agent may be used in membrane resolution method.

In using the resolving agent of the present invention in liquid chromatography, there may be employed a method wherein the powdered resolving agent is packed in a column, a method wherein a capillary column is coated with the resolving agent, a method wherein a capillary is made from the resolving agent to use the inner wall thereof and a method wherein the resolving agent is spun and bundled up to form a column. Among them, the method wherein the powdered resolving agent is employed is most general.

The resolving agent is powdered preferably by crushing or by forming beads. The particle size which varies depending on the size of a column or plate used is 1 μm to 10 μm, preferably 1 to 300 μm. The particles are preferably porous.

It is preferred to support the resolving agent on a carrier so as to improve the durability thereof to pressure, to prevent swelling or shrinkage thereof due to solvent exchange or to reduce the number of theoretical plates. The suitable size of the carrier which varies depending on the size of the column or plate used is generally 1 μm to 10 μm, preferably 1 to 300 μm. The carrier is preferably porous and has an average pore diameter of 10 Å to 100 μm, preferably 50 to 50,000 Å. The amount of the resolving agent to be supported is 1 to 100 wt.%, preferably 5 to 50 wt.%, based on the carrier.

The resolving agent may be supported on the carrier by either chemical or physical means. The physical means includes one wherein the resolving agent is dissolved in a suitable solvent, the resulting solution is mixed with a carrier homogeneously and the solvent is distilled off by means of a gaseous stream under reduced pressure or heating and one wherein the resolving agent is dissolved in a suitable solvent, the resulting solution is mixed homogeneously with a carrier and the mixture is dispersed in a liquid incompatible with said solvent by stirring to diffuse the solvent. The resolving agent thus supported on the carrier may be crystallized, if necessary, by heat treatment or the like. Further, the state of the supported resolving agent and accordingly its re-solving power can be modified by adding a small amount of a solvent thereto to temporarily swell or dissolve it and then distilling the solvent off.

Both porous organic and inorganic carriers may be used, though the latter is preferred. The suitable porous organic carriers are those comprising a high molecular substance such as polystyrene, polyacrylamide or polyacrylate. The suitable porous inorganic carriers are synthetic or natural products such as silica, alumina, magnesia, titanium oxide, glass, silicate or kaolin. They may be surface-treated so as to improve their affinity for the resolving agent. The surface treatment may be effected with an organosilane compound or by plasma polymerization.

In liquid or thin layer chromatography, any developer may be used except those in which the resolving agent is soluble or which are reactive with the resolving agent. In case the resolving agent has been bound to the carrier by the chemical process or it has been insolubilized by crosslinking, any solvent other than a reactive liquid may be used. As a matter of course, it is preferred to select the developer after examination of various developers since the resolving characteristics of chemical substances or optical isomers vary depending on the developer used.

In the thin layer chromatography, a layer having a thickness of 0.1 to 100 mm and comprising the resolving agent in the form of particles of about 0.1 μm to 0.1 mm and, if necessary, a small amount of a binder is formed on a supporting plate.

In the membrane resolution process, the resolving agent is used in the form of a hollow filament or film. (Effects of the invention)

The resolving agent of the present invention containing the polysaccharide having an acyl or carbamoyl substituent as the effective component is effective for the resolution of various compounds. Particularly, it is quite effective for the resolution of optical isomers which are quite difficult to resolve. Either one of the optical isomers to be resolved is selectively adsorbed on the resolving agent.

DETAILED DESCRIPTION OF THE INVENTION

Figure 1:
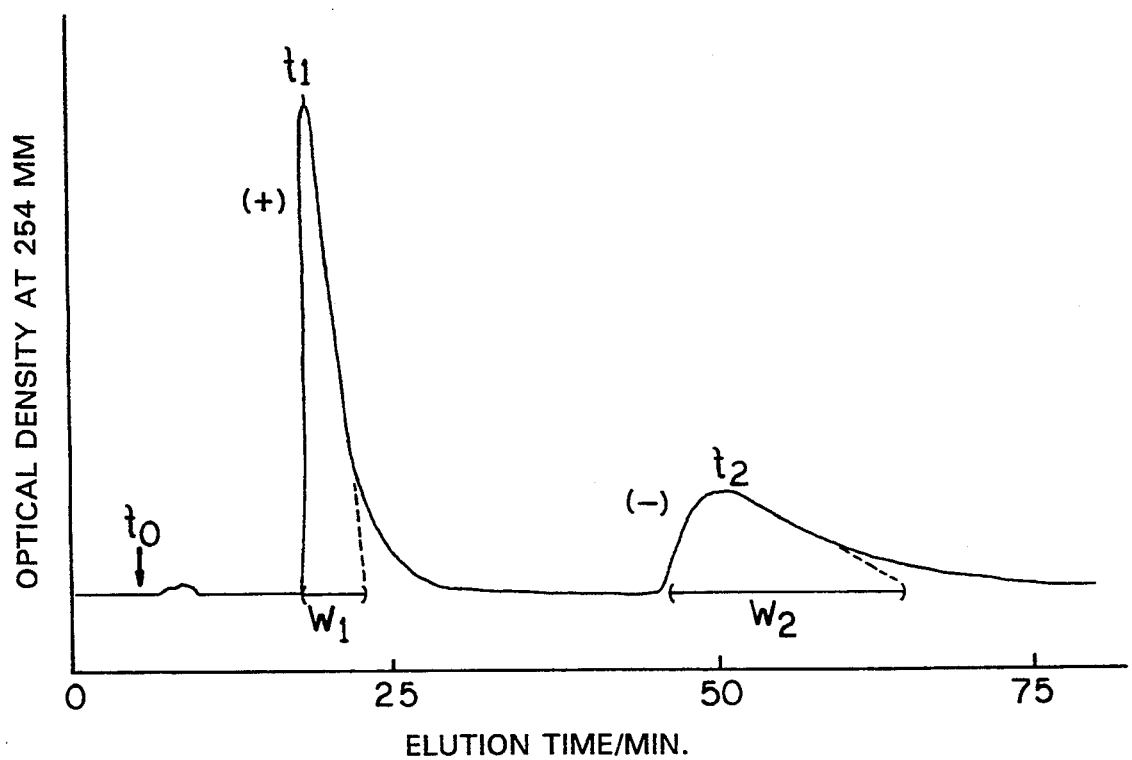
FIG. 1 is a graph showing the chromatographic resolution of transcyclopropanedicarboxylic acid dianilide on a column using an amylose tris(4-styrylphenylcarbamate) packing.

The remarkable effects of the resolving agents of the present invention are apparent from comparison of separation factor $\alpha$ obtained in the following examples with those of conventional cellulose resolving agents.

For example, in the optical resolution of transstilbene oxide according to chromatography using a mixture of hexane and 2-propanol in a ratio of 9:1 as the eluent, the $\alpha$ value obtained when cellulose tri-$\beta$-naphthoate was used was 1.58 which was far higher than the $\alpha$ value of 1.42 obtained when cellulose tribenzoate, i.e., a known cellulose resolving agent, was used. In the optical resolution of Tröger's base, through the highest $\alpha$ value obtainable with known cellulose resolving agents was 1.40 (obtained with tribenzylcellulose, a higher $\alpha$ value can be obtained with the resolving agent of the present invention. More particularly, $\alpha$ values of 2.82, 1.84 and 1.42 are obtained with cellulose tricinnamate, trisbi-phenylcarboxylate and trisphenylazobenzoate, respectively. From this fact, the effects of the substituents in the resolving agent of the present invention are evident.

The following examples will further illustrate the present invention, which by no means limit the invention. In the examples, the terms are defined as follows:

$$\text{capacity ratio } (k') = \frac{\text{retention volume (of enantiomer)} - \text{(void volume)}}{\text{(void volume)}}$$

$$\text{separation factor } (\alpha) = \frac{\text{capacity ratio of enantiomer (adsorbed more strongly)}}{\text{capacity ratio of enantiomer (adsorbed less strongly)}}$$

$$\text{rate of separation } (R_s) = \frac{2 \times \text{distance between a peak of more strongly adsorbed enantiomer and that of less strongly adsorbed enantiomer}}{\text{(total band width of both peaks)}}$$

Synthesis Example 1

10 grams of silica beads (Lichrospher SI 1000; a product of Merck & Co.) was placed in a 200 ml roundbottom flask with a side arm. After vacuum-drying in an oil bath at 120° C. for 3 hours, N₂ was introduced therein. 100 ml of toluene which had been preliminarily distilled in the presence of CaH₂ was added to the silica beads. 3 ml of diphenyldimethoxysilane (KBM 202; a product of Shin'etsu Kagaku Co., Ltd.) was added to the mixture and they were stirred together and then reacted at 120° C. for 1 hour. After distilling off 3 to 5 ml of toluene, the reaction was carried out at 120° C. for 2 hours. The mixture was filtered through a glass filter, washed with 50 ml of toluene three times and then with 50 ml of methanol three times and dried in vacuo at 40° C. for 1 hour.

About 10 grams of the silica beads were placed in the 200 ml round-bottom flask with a side arm. After vacuum drying at 100° C. for 3 hours, the pressure was returned to atmospheric pressure and the mixture was cooled to room temperature. Then, N₂ was introduced therein. 100 ml of distilled toluene was added to the dried silica beads. 1 ml of N, O-bis (trimethylsilyl) acetamide (a trimethylsilylating agent) was added thereto and the mixture was stirred to effect the reaction at 115°

C. for 3 hours. The reaction mixture was filtered through a glass filter, washed with toluene and dried in vacuo for about 4 hours.

Synthesis Example 2

Cellulose triacetate (a product of Daicel Ltd.) having a number-average degree of polymerization of 110 and a degree of substitution of 2.97 was dissolved in 1 liter of acetic acid (a product of Kanto Kagaku Co.). 5.2 ml of water and 5 ml of conc. sulfuric acid were added to the resulting solution and the reaction was carried out at 80° C. for 3 hours. The reaction mixture was cooled and sulfuric acid was neutralized with an excess aqueous magnesium acetate solution. The resulting solution was added to 3 liters of water to precipitate cellulose triacetate having a reduced molecular weight. After filtration and collection with a glass filter (G3), it was dispersed in 1 liter of water. After filtration followed by vacuum drying, the obtained product was dissolved in methylene chloride and reprecipitated from 2-propanol. The dissolution and the reprecipitation were repeated twice to effect the purification. The product was dried. According to the IR and NMR spectra, the product was identified as cellulose triacetate. The number-average molecular weight of the product as determined by vapor pressure osmometry was 7900, which corresponded to the number-average degree of polymerization of 27. The vapor pressure osmometry was conducted with a vapor pressure osmometer Corona 117 using a solvent mixture of chloroform/1% ethanol.

60 grams of the obtained cellulose triacetate was dispersed in 200 ml of 2-propanol. 60 ml of 100% hydrazine hydrate (a product of Nakarai Kagaku Co.) was added dropwise slowly to the dispersion under gentle stirring. The suspension was maintained at 60° C. for 3 hours and the resulting cellulose was filtered through a glass filter, washed with acetone repeatedly and vacuum-dried at 60° C. In the IR spectrum of the product, no absorption band due to the carbonyl group at around 1720 cm$^{-1}$ was observed and the IR spectrum coincided with that of cellulose.

Synthesis Example 3 (Synthesis of cellulose tris-4-biphenylcarboxylate)

10 ml of pyridine and 3 ml of triethylamine were added to 0.7 grams of the cellulose obtained in above Synthesis Example 2, 7.0 grams of 4-biphenylcarbonyl chloride (a product of Aldrich Co.) and 0.02 grams of dimethylaminopyridine. The mixture was kept at 90° C. under stirring for 5 hours. 10 ml of benzene was added thereto and the obtained mixture was kept at 90° C. for 1.5 hours. The dark brown reaction liquid was added to 200 ml of ethanol. The formed precipitates of the cellulose ester were filtered through a glass filter (G3), washed with ethanol and then acetone repeatedly and dried in vacuo to obtain 2.6 grams of the product. In its IR spectrum, characteristic absorptions were observed at 3020, 3050, 1720, 1605, 1260, 1100, 860, 740 and 700 cm$^{-1}$ and no stretching vibration of a hydroxyl group was observed. This fact suggested that the product was a trisubstituted compound.

Synthesis Example 4 (Synthesis of cellulose tris-p-phenylazobenzoate)

51.5 ml of dehydrated pyridine, 5.7 ml of dehydrated triethylamine and 37 mg of 4-dimethylaminopyridine were added to 1.1 grams of the cellulose obtained in Synthesis Example 2. 15.8 grams of p-phenylazobenzoyl chloride was added thereto under stirring and the reaction was carried out at 100° C. for 5 hours. After cooling, the product was added to 400 ml of ethanol under stirring to form precipitates. After filtration through a glass filter, the precipitates were washed thoroughly with ethanol. After drying in vacuo, the product was dissolved in 30 ml of methylene chloride. After removal of insoluble matter, the product was reprecipitated from 400 ml of ethanol. The precipitates were filtered, washed with ethanol, dehydrated and dried to obtain 5.2 grams of cellulose tris-p-phenylazobenzoate. This product was dissolved in methylene chloride and the solution was applied to a sodium chloride tablet and dried. The infrared absorption spectrum of the product had the following characteristic absorption bands:

3050 cm$^{-1}$: stretching vibration of aromatic C—H,
1740 cm$^{-1}$: stretching vibration of C=O of carboxylic acid ester,
1610, 1490, 1450 and 1420 cm$^{-1}$: skeletal vibration due to stretching of carbon and carbon in the benzene ring
1270 cm$^{-1}$: stretching vibration of C—O of ester,
1000 to 1160 cm$^{-1}$: stretching vibration of C—O—C of cellulose
680 to 900 cm$^{-1}$: out-of-plane deformation vibration of benzene ring.

Substantially no absorption at around 3450 cm$^{-1}$ due to OH of cellulose was observed. This fact suggested that the product substantially comprised a trisubstituted compound. In the proton-NMR spectrum determined in CDCl$_3$, the characteristic absorptions were as follows:

6.9 to 8.3 ppm: proton of benzene ring, and
3.0 to 5.7 ppm: protons of the cellulose ring and methylene in position 6.

The ratio of intensities of the absorptions was 27:7.

Synthesis Example 5 (Synthesis of cellulose tricinamate)

70 ml of dehydrated pyridine, 7.7 ml of dehydrated triethylamine and 50 milligrams of 4-dimethylaminopyridine were added to 1.5 grams of the cellulose obtained in Synthesis Example 2. 13.9 grams of cinnamoyl chloride was added to the mixture under stirring and the reaction was carried out at 100° C. for 5 hours. After cooling, the product was added to 400 ml of ethanol under stirring to form precipitates. After filtration through a glass filter, the product was washed thoroughly with ethanol. After vacuum drying, the product was dissolved in 30 ml of methylene chloride. After removal of insoluble matter, the product was reprecipitated from 400 ml of ethanol. The precipitates were filtered, washed with ethanol, dehydrated and dried to obtain 5.0 grams of cellulose cinnamate.

The product was dissolved in methylene chloride and the solution was applied to a sodium chloride tablet and dried. The infrared absorption spectrum of the product had the following characteristic absorption bands:

around 3050 cm$^{-1}$: stretching vibration of olefinic C—H,
1730 cm$^{-1}$: stretching vibration of C=O of carboxylic ester,
1640 cm$^{-m}$: stretching vibration of C=O,
1585, 1500, 1460 cm$^{-1}$: skeletal vibration due to stretching of carbon and carbon in the benzene ring,
1250 cm$^{-1}$: stretching vibration of C—O of ester,
1040 to 1160 cm$^{-1}$: stretching vibration of C—O—C of cellulose, 990 cm$^{-1}$: deformation vibration of olefinic C—H,
675 to 900 cm$^{-1}$: out-of-plane deformation vibration of benzene ring.

Substantially no absorption at around 3450 cm$^{-1}$ due to OH of cellulose was observed. This fact suggested that the product substantially comprised a trisubstituted compound. In the proton NMR spectrum determined in CDCl$_3$, the characteristic absorptions were as follows:

5.9 to 7.8 ppm: proton of cinnamic acid segment, and
3.2 to 5.5 ppm: protons of the glucose ring of cellulose and methylene in position 6.

The ratio of intensities of these absorptions was 3:1.

Synthesis Example 6 (Synthesis of cellulose tri-β-naphthoate)

20 ml of pyridine and 5 ml of triethylamine were added to 1.0 grams of the cellulose obtained in Synthesis Example 2, 10.6 grams of β-naphthoyl chloride (a product of Aldrich Co.) and 0.05 grams of 4-dimethylaminopyridine (a product of Aldrich Co.). The mixture was kept at 80° C. for 2 hours and then at 100° C. for 4 hours. After cooling, the reaction liquid was added to methanol. Precipitates thus formed were filtered, washed with methanol repeatedly and dried in vacuo to obtain 3.85 grams of a product. The product was dissolved in dichloromethane. After filtration through a glass filter (G-3) to remove a small amount of insoluble matter, the product was purified by reprecipitation from methanol. In the IR spectrum, characteristic absorptions were observed at 3060, 1735, 1280, 1230, 1200, 1140, 1100, 795 and 785 cm$^{-1}$ and no stretching vibration of a hydroxyl group at around 3500 cm$^{-1}$ was observed. This fact suggested that the product was a trisubstituted compound.

EXAMPLE 1

1.2 grams of cellulose tris-4-biphenylcarboxylate obtained in Synthesis Example 3 was dissolved in a mixture of 7.5 ml of dichloromethane and 1.0 ml of benzene. After filtration through a glass filter (G3), about 7.5 ml of the solution was absorbed by the silica beads obtained in Synthesis Example 1. The solvent was removed under reduced pressure to obtain a powdery, supported material.

EXAMPLE 2

1.2 grams of cellulose tris-p-phenylazobenzoate obtained in Synthesis Example 4 was dissolved in 7.5 grams of dichloromethane. 7.5 ml of the solution was absorbed by the silica beads obtained in Synthesis Example 1. The solvent was distilled off under reduced pressure to obtain a powdery, supported material.

EXAMPLE 3

1.2 grams of cellulose tricinnamate obtained in Synthesis Example 5 was dissolved in 7.5 ml of dichloromethane. 7.5 ml of the solution was absorbed by the silica beads obtained in Synthesis Example 1. The solvent was distilled off under reduced pressure to obtain a powdery, supported material.

EXAMPLE 4

1.1 g of cellulose tri-β-naphthoate obtained in Synthesis Example 6 was dissolved in 6.9 ml of dichloromethane. 7.0 ml of the solution was absorbed by 3.10 grams of the silica beads obtained in Synthesis Example 1. The solvent was distilled off under reduced pressure to obtain a powdery, supported material.

Application Example 1

The silica beads carrying cellulose tris-4-biphenylcarboxylate obtained in Example 1 were packed in a stainless steel column having a length of 25 cm and an inner diameter of 0.46 cm by slurry process. The high-performance liquid chromatograph used was TRIROTAR-SR (a product of Japan Spectroscopic Co., Ltd.) and the detector used was UVIDEC-V. The results of resolution of various racemic compounds are shown in Table 1.

TABLE 1

| Racemates | Capacity ratio $k_1'$ | Capacity ratio $k_2'$ | Separation factor $\alpha$ | Rate of separation $R_s$ | Flow rate ml/min |
|---|---|---|---|---|---|
| (benzoin-type structure with O bridging two phenyl rings) | 2.44 | 3.20 | 1.31 | 1.65 | 0.5 |
| (2,2'-diaminobinaphthyl / bi-aryl N-N structure) | 2.74 | 5.04 | 1.84 | 1.39 | 0.5 |
| (mandelamide: phenyl-C(OH)(H)-CONH$_2$) | 7.28 | 8.30 | 1.14 | 0.88 | 0.5 |

TABLE 1-continued

| Racemates | Capacity ratio $k_1'$ | $k_2'$ | Separation factor $\alpha$ | Rate of separation Rs | Flow rate ml/min |
|---|---|---|---|---|---|
| 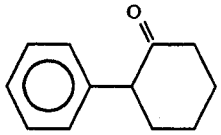 | 4.28 | 4.96 | 1.16 | 0.64 | 0.5 |

Solvent: hexane/2-proponol (9:1)

Application Example 2

The silica beads carrying cellulose trisazobenzenecarboxylate obtained in Example 2 were packed in a stainless steel column having a length of 25 cm and an inner diameter of 0.46 cm by slurry process. The high-performance liquid chromatograph used was TRIROTAR-SR (a product of Japan Spectroscopic Co., Ltd.) and the detector used was UVIDEC-V. The results of resolution of various racemic compounds are shown in Table 2.

Application Example 3

The silica beads carrying cellulose tricinnamate obtained in Example 3 were packed in a stainless steel column having a length of 25 cm and an inner diameter of 0.46 cm by slurry process. The high-performance liquid chromatograph used was TRIROTAR-SR (a product of Japan Spectroscopic Co., Ltd. ) and the detector used was UVIDEC-V. The results of resolution of various racemic compounds are shown in Table 3.

TABLE 2

| Racemates | Capacity ratio $k_1'$ | $k_2'$ | Separation factor $\alpha$ | Rate of separation Rs | Flow rate ml/min |
|---|---|---|---|---|---|
| 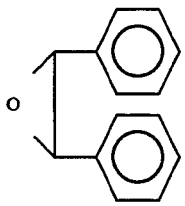 | 1.45 | 1.85 | 1.28 | 1.36 | 0.5 |
| 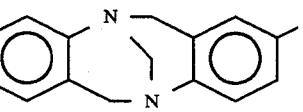 | 1.94 | 2.74 | 1.42 | 1.10 | 0.5 |
| 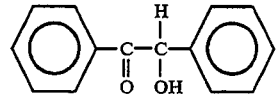 | 4.44 | 5.10 | 1.15 | 0.84 | 0.5 |
| 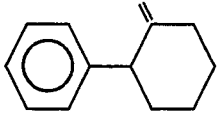 | 3.25 | 3.65 | 1.12 | — | 0.5 |

Solvent: hexane/2-propanol (9:1)

TABLE 3

| Racemates | Capacity ratio $k_1'$ | $k_2'$ | Separation factor $\alpha$ | Rate of separation Rs | Flow rate ml/min |
|---|---|---|---|---|---|
| 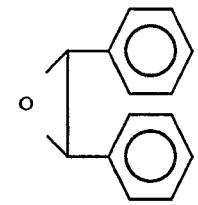 | 2.75 | 3.17 | 1.15 | 1.14 | 0.5 |

TABLE 3-continued

| Racemates | Capacity ratio $k_1'$ | $k_2'$ | Separation factor $\alpha$ | Rate of separation Rs | Flow rate ml/min |
| --- | --- | --- | --- | --- | --- |
| Ph-CH(OH)-C(O)-Ph (benzoin) | 9.64 | 10.4 | 1.08 | 0.8 | 0.5 |
| 1,2-bis(CONHPh)cyclobutane | 5.28 | 8.04 | 1.52 | 0.7 | 0.5 |
| 2-phenylcyclohexanone | 6.19 | 7.77 | 1.26 | 1.88 | 0.5 |
| Troger's base | 4.64 | 13.1 | 2.82 | 3.46 | 0.5 |

Solvent: hexane/2-propanol (9:1)

Application Example 4

The silica beads carrying cellulose tri-β-naphthoate obtained in Example 4 were packed in a stainless steel column having a length of 25 cm and an inner diameter of 0.46 cm by the slurry process. The high-performance liquid chromatograph used was TRIROTAR-SR (a product of Japan Spectroscopic Co., Ltd.) and the detector used was UVIDEC-V. The results of the resolution of trans-stilbene oxide are shown in Table 4.

TABLE 4

| Racemates | Capacity ratio $k_1'$ | $k_2'$ | Separation factor $\alpha$ | Rate of separation Rs | Flow rate ml/min |
| --- | --- | --- | --- | --- | --- |
| trans-stilbene oxide | 2.97 | 4.70 | 1.58 | 1.31 | 0.5 |

Solvent: hexane/2-propanol (9:1)

Synthesis Example 7 (Synthesis of p-chlorocinnamoyl chloride)

100 ml of benzene was added to 18.3 grams of p-chlorocinnamic acid. 12 ml of thionyl chloride was added dropwise slowly thereto at ambient temperature. The temperature was elevated to 80° C. and the heating was continued until foaming ceased. Benzene and thionyl chloride were distilled off and the residue was dried thoroughly under reduced pressure.

Synthesis Example 8 (Synthesis of cellulose tris-p-chlorocinnamate)

1 gram of cellulose obtained in Synthesis Example 2 was dispersed in 50 ml of pyridine. 11.2 grams of p-chlorocinnamoyl chloride was added to the dispersion and the reaction was carried out at 90° C. for 5 hours.

After cooling, the reaction mixture was added to ethanol to form precipitates, which were washed with ethanol and dried in vacuo. The dried product was dissolved in methylene chloride. The solution was filtered through a glass filter (G-3). The filtrate was added to ethanol to form precipitates, which were washed thoroughly with ethanol and dried.

Cellulose p-chlorocinnamate thus obtained was dissolved in methylene chloride. The solution was applied to a rock salt cell and dried. In the IR absorption spectrum, substantially no absorption due to an OH group of cellulose was observed.

Synthesis Example 9 (Synthesis of m-chlorocinnamoyl chloride)

100 ml of benzene was added to 18.3 grams of m-chlorocinnamic acid. 12 ml of thionyl chloride was added dropwise slowly thereto at ambient temperature. The temperature was elevated to 80° C. and the heating was continued until foaming ceased. Benzene and thionyl chloride were distilled off and the residue was dried thoroughly under reduced pressure.

Synthesis Example 10 (Synthesis of cellulose tris-m-chlorocinnamate)

1 gram of cellulose obtained in Synthesis Example 2 was dispersed in 50 ml of pyridine. A solution of 11.2 grams of m-chlorocinnamoyl chloride in 5 ml of benzene was added to the dispersion and the reaction was carried out at 90° C. for 5 hours.

After cooling, the reaction mixture was added to ethanol to form precipitates, which were washed with ethanol and dried in vacuo. The dried product was dissolved in methylene chloride. The solution was filtered through a glass filter (G-3). The filtrate was added to ethanol to form precipitates, which were washed thoroughly with ethanol and dried.

Cellulose m-chlorocinnamate thus obtained was dissolved in methylene chloride. The solution was applied to a rock salt cell and dried. In the IR absorption spectrum, substantially no absorption due to an OH group of cellulose was observed.

Synthesis Example 11 (Synthesis of p-methylcinnamoyl chloride)

100 ml of benzene was added to 16.2 grams of p-methylcinnamic acid. 12 ml of thionyl chloride was added dropwise slowly thereto at ambient temperature. The temperature was elevated to 70° C. and the heating was continued until foaming ceased. Benzene and thionyl chloride were distilled off and the residue was dried thoroughly under reduced pressure.

Synthesis Example 12 (Synthesis of cellulose tris-p-methylcinnamate)

1 gram of the cellulose obtained in Synthesis Example 2 was dispersed in 50 ml of pyridine. 10.1 grams of p-methylcinnamoyl chloride was added to the dispersion and the reaction was carried out at 95° C. for 5 hours.

After cooling, the reaction mixture was added to ethanol to form precipitates, which were washed with ethanol and dried in vacuo. The dried product was dissolved in methylene chloride. The solution was filtered through a glass filter (G-3). The filtrate was added to ethanol to form precipitates, which were washed thoroughly with ethanol and dried.

Cellulose p-methylcinnamate thus obtained was dissolved in methylene chloride. The solution was applied to a rock salt cell and dried. In the IR absorption spectrum, substantially no absorption due to an OH group of cellulose was observed.

Synthesis Example 13 (Synthesis of p-methoxycinnamoyl chloride)

100 ml of benzene was added to 17.8 grams of p-methoxycinnamic acid. 12 ml of thionyl chloride was added dropwise slowly thereto at ambient temperature. The temperature was elevated to 70° C. and the heating was continued until foaming ceased. Benzene and thionyl chloride were distilled off and the residue was dried thoroughly under reduced pressure.

Synthesis Example 14 (Synthesis of cellulose tris-p-methoxycinnamate)

1 gram of cellulose obtained in Synthesis Example 2 was dispersed in 50 ml of pyridine. 10.9 grams of p-methoxycinnamoyl chloride was added to the dispersion and the reaction was carried out at 95° C. for 5 hours.

After cooling, the reaction mixture was added to ethanol to form precipitates, which were washed with ethanol and dried in vacuo. The dried product was dissolved in methylene chloride. The solution was filtered through a glass filter (G-3). The filtrate was added to ethanol to form precipitates, which were washed thoroughly with ethanol and dried.

Cellulose p-methoxycinnamate thus obtained was dissolved in methylene chloride. The solution was applied to a rock salt cell and dried. In the IR absorption spectrum, substantially no absorption due to an OH group of cellulose was observed.

Synthesis Example 15 (Synthesis of G-cyanocinnamoyl chloride)

100 ml of benzene was added to 17.3 grams of α-cyanocinnamic acid. 12 ml of thionyl chloride was added dropwise slowly thereto at ambient temperature. The temperature was elevated to 70° C. and the heating was continued until foaming ceased. Benzene and thionyl chloride were distilled off and the residue was dried thoroughly under reduced pressure.

Synthesis Example 16 (Synthesis of cellulose tris-α-cyanocinnamate)

1 gram of the cellulose obtained in Synthesis Example 2 was dispersed in 50 ml of pyridine. 10.6 grams of α-cyanocinnamoyl chloride was added to the dispersion and the reaction was carried out at 95° C. for 5 hours.

After cooling, the reaction mixture was added to ethanol to form precipitates, which were washed with ethanol and dried in vacuo. The dried product was dissolved in methylene chloride. The solution was filtered through a glass filter (G-3). The filtrate was added to ethanol to form precipitates, which were washed thoroughly with ethanol and dried.

Cellulose α-cyanocinnamate thus obtained was dissolved in methylene chloride. The solution was applied to a rock salt cell and dried. In the IR absorption spectrum, substantially no absorption due to an OH group of cellulose was observed.

Synthesis Example 17 (Synthesis of 3-(2-thienyl)acryloylchloride)

65 ml of benzene was added to 10 grams of 3-(2-thienyl)acrylic acid. 7.8 ml of thionyl chloride was added dropwise slowly thereto at ambient temperature. The temperature was elevated to 70° C. and the heating was continued until foaming ceased. Benzene and thionyl chloride were distilled off and the residue was dried thoroughly under reduced pressure.

Synthesis Example 18 (Synthesis of cellulose tris-3-(2-thienyl)acrylate)

1 gram of the cellulose obtained in Synthesis Example 2 was dispersed in 50 ml of pyridine. 9.6 grams of 3-(2-thienyl)acryoyl chloride was added to the dispersion and the reaction was carried out at 95° C. for 5 hours.

After cooling, the reaction mixture was added to ethanol to form precipitates, which were washed with ethanol and dried in vacuo. The dried product was dissolved in methylene chloride. The solution was filtered through a glass filter (G-3). The filtrate was added to ethanol to form precipitates, which were washed thoroughly with ethanol and dried.

Cellulose 3-(2-thienyl)acrylate thus obtained was dissolved in methylene chloride. The solution was applied to a rock salt cell and dried. In the IR absorption spectrum, substantially no absorption due to an OH group of cellulose was observed.

Synthesis Example 19 (Synthesis of 3-(3-pyridyl)-acryloyl chloride hydrochloride)

67 ml of benzene was added to 10 grams of 3-(3-pyridyl)-acrylic acid. 8.1 ml of thionyl chloride was added dropwise slowly thereto at ambient temperature. The temperature was elevated to 70° C. and the heating was continued until foaming ceased. Benzene and thionyl chloride were distilled off and the residue was dried thoroughly under reduced pressure.

Synthesis Example 20 (Synthesis of cellulose tris-3-(3-pyridyl)acrylate)

1 gram of the cellulose obtained in Synthesis Example 2 was dispersed in 50 ml of pyridine. 11.3 grams of 3-(3-pyridyl)acryloyl chloride hydrochloride was added to the dispersion and the reaction was carried out at 95° C. for 5 hours.

After cooling, the reaction mixture was added to ethanol to form precipitates, which were washed with ethanol and dried in vacuo. The dried product was dissolved in methylene chloride. The solution was filtered through a glass filter (G-3). The filtrate was added to ethanol to form precipitates, which were washed thoroughly with ethanol and dried.

Cellulose 3-(3-pyridyl)acrylate thus obtained was dissolved in methylene chloride. The solution was applied to a rock salt cell and dried. In the IR absorption spectrum, substantially no absorption due to an OH group of cellulose was observed.

Synthesis Example 21 (Synthesis of amylose tricinnamate)

1.8 grams of Amylose DEX-III (a product of Hayashibara Biochem. Lab. Inc.) (degree of polymerization: 100) was added to 10 ml of water. Two drops of a 0.1N aqueous NaOH solution and two drops of ethanol were added to the mixture. The mixture was heated to 50° C. for 30 min, neutralized with acetic acid and added to ethanol to form precipitates, which were washed with ethanol and dried in vacuo.

1.5 grams of the dried amylose was dispersed in a mixture of 70 ml of pyridine, 7.7 ml of triethylamine and 50 milligrams of 4-dimethylaminopyridine. 13.9 grams of cinnamoyl chloride was added to the dispersion and the reaction was carried out at 95° to 100° C. for 5 hours. After cooling, the reaction mixture was added to ethanol to form precipitates, which were washed with ethanol and dried. The dried sample was dissolved in methylene chloride. The solution was filtered through a glass filter (G-3). The filtrate was added to ethanol to form precipitates, which were washed with ethanol and dried in vacuo.

The dried amylose cinnamate was dissolved in methylene chloride. The solution was applied to a rock salt cell and dried. In IR absorption spectrum, substantially no absorption due to an OH group of cellulose was observed.

EXAMPLES 5, 6, 7, 8, 9, 10, 11 AND 12

1.2 grams of each of the polysaccharide ester derivatives obtained in Synthesis Examples 8, 10, 12, 14, 16, 18, 20 and 21 was dissolved in 7.5 ml of dichloromethane. The solution was filtered through a glass filter (G-3) and the filtrate was mixed thoroughly with 3.5 grams of the silica beads obtained in Synthesis Example 1 (the amount of the silica beads being 3.0 grams in Example 12). Dichloromethane was distilled off under reduced pressure to obtain a powdery, supported material.

Application Examples 5, 6, 7, 8, 9, 10, 11 and 12

Each of the supported materials obtained in Examples 5, 6, 7, 8, 9, 10, 11 and 12 was packed in a column in the same manner as in Application Example 1. The optical resolution was conducted by liquid chromatography with the obtained column. The optically resolved compounds and separation factors α of the optical isomers of them are shown in Table 6. The eluent used in the resolution was a mixture of hexane and 2-propanol (9:1), the flow rate was 0.5 ml/min and the analysis temperature was 20° to 25° C.

TABLE 5

| Example | Polysaccharide derivative Compound | Synthesis Ex. |
|---|---|---|
| 5 | cellulose tris-p-chlorocinnamate | 8 |
| 6 | cellulose tris-m-chlorocinnamate | 10 |
| 7 | cellulose tris-p-methoxycinnamante | 12 |
| 8 | cellulose tris-p-methoxycinnamate | 14 |
| 9 | cellulose tris-α-cyanocinnamate | 16 |
| 10 | cellulose tris-3-(2-thienyl)acrylate | 18 |
| 11 | cellulose tris-3-(3-pyridyl)acrylate | 20 |
| 12 | amylose tricinnamate | 21 |

TABLE 6

| Application Example | Resolving agent Effective component | Ex. | Compound | α |
|---|---|---|---|---|
| 5 | cellulose tris-p-chlorocinnamate | 5 | benzoin | 1.11 |
|   |   |   | mandelamide | 1.06 |
| 6 | cellulose tris-m-chlorocinnamate | 6 | t-stilbene oxide | 1.12 |
| 7 | cellulose tris-p-methylcinnamate | 7 | Tröger's base | 1.78 |
| 8 | cellulose tris-p-methoxycinnamate | 8 | Tröger's base | 3.63 |
|   |   |   | benzoin | 1.17 |
|   |   |   | ethotoin* | 1.23 |
| 9 | cellulose tris-α-cyanocinnamate | 9 | t-stilbene oxide | 1.14 |
| 10 | cellulose tris-3-(2-thienyl)-acrylate | 10 | Tröger's base | 2.41 |
| 11 | cellulose tris-3-(3-pyridyl)-acrylate | 11 | Tröger's base | 1.54 |
|   |   |   | methyl α-[4-(4'-fluorophenoxy)phenoxy]propionate** | 1.12 |

*Structure of ethotoin:

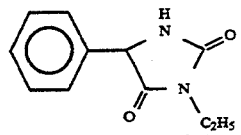

**Structure of methyl α-[4-[4'-fluorophenoxy)phenoxy]propionate:

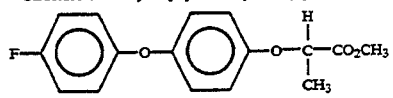

Synthesis Example 22 (Synthesis of curdlan tricinnamate)

4 grams of curdlan triacetate was suspended in 9 ml of 2-propanol and, after adding 3.0 ml of 100% hydrazine hydrate, the mixture was kept at 70° C. for 4.5 hours. The formed curdlan was filtered, washed with 2-propanol twice and then with acetone three times and dried.

1.5 grams of the obtained curdlan was dispersed in a mixture of 70 ml of pyridine, 7.7 ml of triethylamine, and 50 milligrams of 4-dimethylamino-pyridine and, after adding 13.9 grams of cinnamoyl chloride, the mixture was reacted at 100° C. for 5 hours. After cooling, the reaction mixture was poured into ethanol to precipitate curdlan cinnamate. The precipitate was washed with ethanol, dried and dissolved in methylene chloride. The solution was filtered through a glass filter (G-3) and poured into ethanol. The formed precipitate was washed well with ethanol and dried in vacuo. The dried sample was dissolved in methylene chloride, and the solution was applied to a rock salt cell and dried. The infrared absorption spectrum of the curdlan cinnamate showed hardly any absorption assigned to unreacted OH.

EXAMPLE 13

1.2 grams of the curdlan cinnamate obtained in Synthesis Example 22 was dissolved in 7.5 ml of dichloromethane and after filtering the solution through a glass filter (G-3), the filtrate was mixed with 3.5 grams of the silica beads obtained in Synthesis Example 1. The solvent was distilled off in vacuo to obtain a powdery supported resolving agent.

Application Example 13

When ($\pm$) benzoin was optically resolved in the same way as in Application Example 1 by using the supported agent obtained in Example 13, the magnitude of the separation factor ($\alpha$), 1.22 was attained and the dextrorotatory enantiomer eluted first (eluent: hexane and 2-propanol at 9:1).

Synthesis Example 23 (Synthesis of cellulose tris(4-styrylphenylcarbamate))

20.45 grams of p-nitrophenylacetic acid, 12.21 grams of benzaldehyde and 4.6 ml of piperidine were placed in a 100-ml short-neck Kjeldahl flask. An Allihn condenser was attached to the flask and the flask was placed in an oil bath to conduct the reaction at 155° C. for 7 hours. The liquid which was yellow in the initial stage of the reaction turned black in the final stage. The liquid was converted into black crystals when the temperature was lowered to room temperature. The 4-nitrostilbene product was thoroughly washed with acetic acid, filtered through a glass filter, dried in a vacuum line in a desiccator for 3 hours and dried in vacuo at 60° C. for 2 hours.

330 ml of acetic acid and 87.95 grams of tin(II) chloride were placed in a 1-1 three-necked flask. Hydrogen chloride was introduced thereinto for 2 hours. When the turbidity of the solution was reduced, 14.53 grams of 4-nitrostilbene prepared in the above-described step was added thereto. Immediately a violent exothermic reaction occurred and the milky solution was converted into a light green turbid solution. The reaction was continued for additional about one hour and the reaction mixture was left to stand overnight. The solution had an upper yellow liquid layer and a lower layer having green precipitates. The product was heated at 100° C. in an oil bath for about 1.5 hours, filtered through a Buchner funnel, dried in a vacuum line in a desiccator for 2 hours and then dried in vacuo at 60° C. for 2 hours. After drying, 1 liter of a 3 mol/liter aqueous KOH solution was added thereto and the mixture was heated at 100° C. in an oil bath. Cream-colored fluffy precipitates thus formed were separated by filtration through a glass filter, thoroughly washed with an aqueous KOH solution and pure water and then dissolved in diethyl ether. The liquid layer was dried over calcium chloride. The solvent was removed with an evaporator. The 4-aminostilbene product was recrystallized from ethanol, dried in a vacuum line in a dessicator for 2 hours and dried in vacuo at 60° C. for 2 hours.

200 ml of toluene was placed in a 1-liter three-necked flask. Phosgene formed by adding fuming sulfuric acid to carbon tetrachloride under stirring and under reflux of carbon tetrachloride was introduced thereinto. After the inside of the flask was thoroughly purged with phosgene, a solution of 8.26 grams of 4-aminostilbene prepared in the above step in 300 ml of toluene was added dropwise thereto and the temperature was gradually elevated to conduct the reaction under reflux of toluene. The reaction time was 4 hours. Phosgene was introduced thereinto for additional about 30 minutes and then nitrogen was introduced thereinto for about 1 hour. The reaction solution was yellow and clear. Toluene was removed by atmospheric distillation followed by vacuum distillation (38 mmHg, 35° C.) to give cream-colored crystals of 4-aminostilbene.

0.60 grams of cellulose and 50 ml of pyridine were placed in a 100-ml short-neck Kjeldahl flask and about 20 ml of pyridine was distilled off under atmospheric pressure. 3.76 grams of 4-aminostyrylphenyl isocyanate prepared in the above step was added thereto. An Allihn condenser equipped with a calcium chloride tube was attached thereto and the reaction was conducted at 100° C. in an oil bath for 21 hours. The reaction solution was poured into methanol and the crystals thus formed were separated by filtration through a glass filter, dried in a vacuum line in a desiccator and dried in vacuo at 50° C. for 2 hours to yield cellulose tris(4-styrylphenylcarbamate).

Synthesis Example 24 (Synthesis of cellulose tris(4-biphenylylcarbamate))

About 200 ml of toluene was placed in a 1-liter three-necked flask and phosgene was introduced thereinto under cooling. A solution of 25 grams of 4-aminobiphenyl in 200 ml of toluene was added dropwise thereto. The temperature was gradually elevated and the reaction was conducted under a reflux of toluene for 2 hours. The reaction liquid turned reddish purple. The toluene was removed by atmospheric distillation followed by vacuum distillation (38 mmHg, 31° C.). The liquid was red and turned into a gray solid at room temperature. The grey solid was 4-biphenylyl isocyanate.

60 ml of pyridine and 0.72 grams of cellulose were placed in a 100-ml short-neck Kjeldahl flask and an Allihn condenser equipped with a calcium chloride tube was attached thereto. After stirring at 100° C. in an oil bath for 14 hours, about 30 ml of pyridine was distilled off under atmospheric pressure. 3.92 grams of 4-biphenylyl isocyanate was added thereto and the mixture was reacted at 100° C. in the oil bath for 18 hours. The reaction solution was poured into methanol and the cellulose tris(4-biphenylylcarbamate) product thus precipitated was separated by filtration through a glass filter, dried in a vacuum line in a desiccator for 2 hours and dried in vacuo at 50° C. for 2 hours.

Synthesis Example 25 (Synthesis of amylose tris(4-styrylphenylcarbamate))

60 ml of pyridine and 0.62 grams of amylose were placed in a 100-ml short-necked Kjeldahl flask and an Allihn condenser equipped with a calcium chloride tube was attached thereto. After stirring at 100° C. in an oil bath for 12 hours, about 30 ml of pyridine was distilled off under atmospheric pressure. 3.78 grams of 4-aminostilbene was added thereto and the mixture reacted at 100° C. in the oil bath for 24 hours. The reaction solution was poured into methanol and the product thus precipitated was separated by filtration through a glass filter, dried in a vacuum line in a desiccator for 2 hours and then dried in vacuo at 40° C. for 2 hours.

Synthesis Example 26 (Synthesis of amylose tris(4-biphenylylcarbamate ))

60 ml of pyridine and 0.72 grams of amylose were placed in a 100 ml short-necked Kjeldahl flask and an Allihn condenser equipped with a calcium chloride tube was attached thereto. After stirring at 100° C. in an oil bath for 13 hours, about 30 ml of pyridine was distilled off under atmospheric pressure. 3.90 grams of 4-biphenylyl isocyanate was added thereto and the mixture was subjected to the reaction at 100° C. in the oil bath for 20 hours. The reaction solution was poured into methanol and the amylose tris(4-biphenylylcarbamate) product thus precipitated was separated by filtration through a glass filter, dried in a vacuum line in a desiccator for 2 hours and then dried in vacuo at 50° C. for 3 hours.

The results of the elemental analysis of the triphenylcarbamate derivatives of Synthesis Examples 23–26 are shown in Table 7. It is apparent from this table that the analytical values were substantially equal to the calculated ones and, therefore, the hydroxyl groups of the cellulose or amylose had been replaced with the carbamate groups almost quantitatively. In the IR spectra, an absorption due to the stretching vibration of NH of the carbamate group was observed at around 3300 cm$^{-1}$ and that due to the stretching vibration of C=O was observed at around 1750 cm$^{-1}$ to prove that the reaction had been completed.

TABLE 7

Analytical Data of Triphenylcarbamate Derivatives

| | elemental analysis[a] | | | |
|---|---|---|---|---|
| | C % | H % | N % | $[\alpha]_D^{25}$ |
| cellulose tris-(4-styrylphenyl-carbamate) | 73.47 (74.18 | 5.45 5.21 | 4.93 5.09 | +58.9[c] |
| cellulose tris-(4-biphenylyl-carbamate) | 71.45 (71.29 | 5.10 4.95 | 5.53 5.62 | −16.1[b] |
| amylose tris-(4-styrylphenyl-carbamate) | 73.76 (74.18 | 5.35 5.21 | 5.09 5.09 | −409[c] |
| amylose tris-(4-biphenylyl carbamate) | 71.48 (72.29 | 5.07 4.95 | 5.54 5.62 | −266[b] |

[a]calculated values of elemental analysis are shown in parentheses
[b]in tetrahydrofuran
[c]in N,N-dimethylacetamide Synthesis Example 27 (Synthesis of cellulose tris[4-2-phenylethynyl)phenylcarbamate])

An Allihn condenser was attached to a 500-ml three-necked flask and the inside of the flask was purged with nitrogen. 80-ml of Et$_2$NH, 15.2 milligrams (6.79×10$^{-5}$ mol) of Pd(CH$_3$CO$_2$)$_2$, 33.7 milligrams (1.24×10$^{-4}$ mol) of P(Ph)$_3$, 9.96 grams (49.3 mmol) of

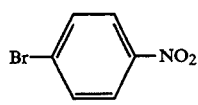

and 8.37 grams (81.9 mmol) of

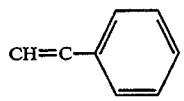

were placed therein and the flask was heated in an oil bath in a nitrogen atmosphere. The reaction solution was black and bubbled violently at a bath temperature of around 90° C. to increase the viscosity thereof. The reaction was conducted at 100° C. for 4 hours.

The three-necked flask was cooled in ice and 200-ml of 3N HCl was slowly added thereto. Brown precipitates thus formed were separated by filtration and subjected to extraction with a mixture of about 170-ml of benzene with 50-ml of water by means of a 500-ml separatory funnel twice. The solvent was removed from the benzene layer by evaporation and the residue was dried at a constant temperature of 50° C. for 2 hours. After recrystallization from 137-ml of ethanol/water (5:2), the nitrotolan product was dried at a constant temperature of 50° C. for 2 hours.

34.5 g of Zn powder and a solution of 5.88 grams of nitrotolan in 760-ml of EtOH were placed in a 1-liter short-neck Kjeldahl flask and an Allihn condenser was attached thereto. 136 grams of a concentrated aqueous HCl solution (35%) was added dropwise thereto over 1.5 hours and the mixture was stirred for 2.5 hours. A precipitate thus formed was separated by filtration and an aqueous KOH solution was added to the filtrate until the pH was increased to about 10. A precipitate thus formed was subjected to the extraction with 300-ml of benzene and 50-ml of water twice. The benzene layer was dried over Na$_2$SO$_4$ overnight. The solvent was removed by evaporation. After filtration through a glass filter, the p-aminotolan product was dried at a constant temperature of 40° C. for 3 hours.

11.06 grams of p-aminotolan was dissolved in 300-ml of toluene. Separately, 100-ml of fuming sulfuric acid was added dropwise slowly to 205-ml of carbon tetrachloride under reflux to form phosgene. After the inside of the reactor had been sufficiently purged with phosgene, the solution of p-aminotolan in toluene was added dropwise thereto. The temperature was slowly elevated to conduct the reaction under a reflux of toluene. The reaction time was 4 hours. After the completion of the reaction, a major part of the toluene was distilled off under atmospheric pressure. Then toluene was removed by vacuum distillation at 28.5° C. under 20 mmHg. The isocyanate could not be distilled off and brown crystals remained.

0.74 grams of cellulose was stirred in 80-ml of pyridine at 100° C. for 1 hour. About 40-ml of pyridine was distilled off. 4.53 grams of the isocyanate was added to the residue and the reaction was conducted at 100° C. for 17 hours. The reaction mixture was poured into methanol to form a precipitate. After stirring for 2 hours, the mixture was filtered through a glass filter. The cellulose tris[4-(2-phenylethynyl)phenylcarbamate] product was dried at a constant temperature of 50° C. for 2 hours.

The results of the elemental analysis of the cellulose tris[4-(2-phenylethynylphenylcarbamate)] of Synthesis Example 27 are shown in Table 8. It is apparent from this table that the analytical values were substantially equal to the calculated values and, therefore, the hydroxyl groups of the cellulose had been replaced with the carbamate groups almost quantitatively.

TABLE 8
Elemental Analysis of Cellulose Tris[4-(2-phenyl-ethynylphenylcarbamate)]

|  | C % | H % | N % |
|---|---|---|---|
| Found | 74.05 | 4.65 | 5.07 |
| Calculated | 74.71 | 4.55 | 5.12 |

$[\alpha]_D^{25} = +35.59°$.

Synthesis Example 28 (Synthesis of cellulose tris(4-phenoxyphenylcarbamate))

25 grams of commercially available 4-phenoxyaniline was dissolved in 700 ml of toluene. A supernatant liquid thus formed was separated by decantation and used in the reaction.

100 ml of fuming sulfuric acid was added slowly and dropwise to 270 ml of carbon tetrachloride under reflux and stirring to form phosgene. After the inside of the device was thoroughly purged with phosgene, a solution of 4-phenoxyaniline in toluene was added dropwise thereto and the temperature was gradually elevated. The reaction was conducted under a reflux toluene for 4 hours.

After the completion of the reaction, a major part of the toluene was distilled off under atmospheric pressure and then 4-phenoxyphenyl isocyanate was distilled off at 120° C. under reduced pressure of 0.358 mmHg. The isocyanate was in the form of a transparent liquid.

0.75 grams of cellulose was stirred in 60 ml of pyridine at 100° C. for 1 hour. Then about 30 ml of pyridine was distilled off under atmospheric pressure. 4.43 grams of 4-phenoxyphenyl isocyanate was added thereto and the reaction was conducted at 100° C. for hours. The reaction mixture was poured into 300 ml of methanol to form a white precipitate. After stirring for about 1 hour, the mixture was filtered through a glass filter. The cellulose tris(4-phenoxyphenylcarbamate) product was dried in a vacuum line in a desiccator for 1.5 hours and then at a constant temperature of 50° C. for 2 hours.

Elemental analysis:

|  | C % | H % | N % |
|---|---|---|---|
| Found | 66.75 | 4.71 | 5.20 |
| Calculated | 67.91 | 4.69 | 5.28 |

Synthesis Example 29 (Synthesis of amylose tris(4-phenoxyphenylcarbamate))

0.77 grams of amylose was stirred in 65 ml of pyridine at 100° C. for 4 hours. Then about 30 ml of pyridine was distilled off under atmospheric pressure. 4.53 grams of 4-phenoxyphenyl isocyanate was added thereto and the reaction was conducted at 100° C. for 24 hours. The reaction mixture was poured into 300 ml of methanol to form a white precipitate. After stirring for several hours, the mixture was filtered through a glass filter. The product was dried in a vacuum line in a desiccator for 1 hour and then at a constant temperature of 60° C. for about 2 hours. The elemental analysis of the amylose tris(4-phenoxyphenylcarbamate) is shown in Table 9. The closeness of the numbers between the analytical values and the calculated values indicate that the hydroxy groups of the amylose have been replaced with the carbamate groups almost quantitatively.

TABLE 9

|  | C % | H % | N % |
|---|---|---|---|
| Found | 66.40 | 4.68 | 5.18 |
| Calculated | 67.91 | 4.69 | 5.28 |

Synthesis Example 29 (Surface treatment of silica gel)

30 grams of silica gel (Lichrospher Si 4000) was dried in vacuo at around 180° C. for 2 hours. 180 ml of benzene was dried by simple distillation over metallic sodium, 6 ml of γ-aminopropyltriethoxysilane and 1.8 ml of pyridine were added thereto and the mixture was heated under reflux in a nitrogen stream for 16 hours. The reaction mixture was poured into methanol, filtered through a glass filter and dried.

EXAMPLE 14

The cellulose or amylose triphenyl derivatives of Synthesis Examples 23–26 were dissolved in about 15 ml of N,N-dimethylacetamide. About 3 ml of the solution was added to the surface-treated silica gel having a large pore diameter and shaken well to uniformly wet the silica gel, which was dried in vacuo at about 60° C. This operation was repeated to cause the silica gel to support the polymer.

The packing material prepared in the above step was subjected to particle size classification with hexane/2-propanol (90:10). It was then packed in a stainless steel column having a length of 25 cm and an inner diameter of 0.46 cm by the slurry packing method.

JASCO TRIROTOR-II was used in HPLC. The detector and polarimeter used were UV (JASCO UV DIC-100-III) and JASCO DIP-181C, respectively. The optical activity was determined with a flow cell having a size of 5 cm×0.2 cm. The eluents used were hexane/2-propanol (IPA) (90/10), hexane/IPA/chloroform (90/5/5), hexane/IPA/chloroform (85/5/10), hexane/IPA/chloroform (75/5/20) and hexane/IPA/chloroform (78/2/20). The flow rate and temperature were 0.5 ml/min and 25° C., respectively.

The following six racemic compounds were used in the optical resolution: benzoin (5), transstilbene oxide (6), 6,6'-dimethyl-2,2'-biphenyldiol (7), transcyclopropanedicarboxylic dianilide (8), 1,2,2,2-tetraphenylethanol (9) and Tröger's base (10 ).

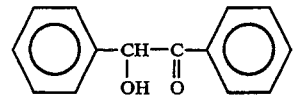

5

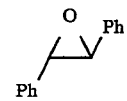

6

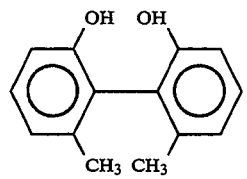

7

8

-continued

9 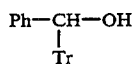

10 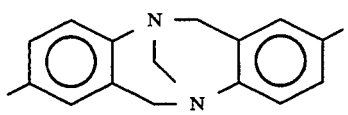

The separation factors α on the cellulose and amylose triphenylcarbamate derivatives and cellulose and amylose triphenylcarbamate obtained when hexane-2-propanol (90:10) was used as the eluent are shown in Table 10.

Cellulose tris(4-biphenylylcarbamate) behaved as a liquid crystal in THF. Although other triphenylcarbamate derivatives did not behave as a liquid crystal, they were crystalline.

The compounds 1 to 4 had a poor solubility in solvents and were scarcely soluble also in chloroform. Chloroform was added to the eluent to vary the composition thereof in the optical resolution. The results of using cellulose tris(4-styrylphenylcarbamate), cellulose tris(4-biphenylylcarbamate), amylose tris(4-styrylphenylcarbamate) and amylose tris(4-biphenylylcarbamate) as separating agents for the above-mentioned six racemic compounds are shown in Tables 11-14 respectively. FIG. 1 shows the chromatographic resolution of transcyclopropane dicarboxylic acid on a column using an amylose tris(4-styrylphenylcarbamate) packing.

TABLE 11

| Cellulose tris(4-styrylphenylcarbamate) | | | | | |
|---|---|---|---|---|---|
| | Racemic Compound 5 | | Racemic Compound 6 | | |
| | k1 | α | k1 | α | Rs |
| Hex:IPA 90:10 | 3.54(+) | 1.05 | 0.70(+) | 1.22 | 0.88 |
| Hex:IPA:CHCl₃ | 3.11(+) | ~1 | 0.59(+) | 1.20 | 0.76 |

TABLE 10

Separation factors (α) on cellulose and amylose triphenylcarbamate derivatives

| Racemic Compounds | X = | Cellulose derivatives Ph-CH=CH- 1 | Cellulose derivatives Ph- 2 | Cellulose derivatives H— | Amylose derivatives Ph-CH=CH- 3 | Amylose derivatives Ph- 4 | Amylose derivatives H— |
|---|---|---|---|---|---|---|---|
| 5 Ph-CH(OH)-CO-Ph | | 1.05 | 1 | 1 | 1.20 | 1.23 | 1 |
| 6 (binaphthol-type diol with CH₃) | | 1.31 | 1.35 | 1.65 | 1.13 | 1.35 | 1.53 |
| 8 cyclopropane-CONHPh/CONHPh | | 1 | 1.31 | 1.45 | 2.53 | 2.48 | 1.52 |
| 9 Ph-CH(OH)-Tr | | 1 | 1.20 | 1.22 | 1.31 | 1.49 | 1.84 |
| 10 (dibenzodiazepine) | | 1.19 | 1.25 | 1.37 | 1.09 | 1.12 | 1.2 |

Eluent, hexan-2-propanol (90:10)

TABLE 11-continued

Cellulose tris(4-styrylphenylcarbamate)

| 90:5:5 | | | | | |
|---|---|---|---|---|---|
| Hex:IPA:CHCl₃ 85:5:10 | 2.39(+) | ~1 | 0.46(+) | 1.21 | 0.77 |
| Hex:IPA:CHCl₃ 75:5:20 | 1.31(+) | ~1 | 0.58(+) | 1.11 | |
| Hex:IPA:CHCl₃ 78:2:20 | 2.00(+) | ~1 | 0.31(+) | 1.23 | |

| | Racemic Compound 7 | | | Racemic Compound 8 | | |
|---|---|---|---|---|---|---|
| | k1 | α | Rs | k1 | α | Rs |
| Hex:IPA 90:10 | 1.13(−) | 1.31 | 0.94 | 1.73(−) | ~1 | |
| Hex:IPA:CHCl₃ 90:5:5 | 1.63(−) | 1.26 | 0.80 | 3.49(−) | 1.13 | |
| Hex:IPA:CHCl₃ 85:5:10 | 1.25(−) | 1.25 | 0.71 | 2.60(−) | 1.26 | |
| Hex:IPA:CHCl₃ 75:5:20 | 0.91(−) | 1.20 | 0.72 | 2.34(−) | 1.22 | 0.59 |
| Hex:IPA:CHCl₃ 78:2:20 | 2.07(−) | 1.13 | 0.47 | 11.00(−) | | |

| | Racemic Compound 9 | | | Racemic Compound 10 | | |
|---|---|---|---|---|---|---|
| | k1 | α | Rs | k1 | α | Rs |
| Hex:IPA 90:10 | 1.23(+) | ~1 | | 1.17(+) | 1.19 | 0.66 |
| Hex:IPA:CHCl₃ 90:5:5 | 1.16(+) | 1.12 | | 1.02(+ | 1.22 | 0.80 |
| Hex:IPA:CHCl₃ 85:5:10 | 0.87(+) | 1.17 | | 0.65(+) | 1.24 | 0.75 |
| Hex:IPA:CHCl₃ 75:5:20 | 0.49(+) | 1.19 | | 0.37(+) | 1.25 | |
| Hex:IPA:CHCl₃ 78:2:20 | 0.76(+) | 1.25 | 0.81 | 2.74(+) | 1.20 | 1.07 |

TABLE 12

Cellulose tris(4-biphenylylcarbamate)

| | Racemic Compound 5 | | | Racemic Compound 6 | | |
|---|---|---|---|---|---|---|
| | k1 | α | Rs | k1 | α | Rs |
| Hex:IPA 90:10 | 4.88(−) | ~1 | | 0.72(+) | 1.41 | 1.23 |
| Hex:IPA:CHCl₃ 90:5:5 | 4.71(−) | ~1 | | 0.52(+) | 1.40 | 1.29 |
| Hex:IPA:CHCl₃ 85:5:10 | 3.18(−) | ~1 | | 0.44(+) | 1.34 | 1.03 |
| Hex:IPA:CHCl₃ 75:5:20 | 1.51(−) | ~1 | | 0.58(+) | 1.17 | |
| Hex:IPA:CHCl₃ 78:2:20 | 2.78(−) | ~1 | | 0.32(+) | 1.37 | 0.96 |

| | Racemic Compound 7 | | | Racemic Compound 8 | | |
|---|---|---|---|---|---|---|
| | k1 | α | Rs | k1 | α | Rs |
| Hex:IPA 90:10 | 1.38(−) | 1.35 | 0.95 | 1.90(−) | 1.31 | |
| Hex:IPA:CHCl₃ 90:5:5 | 1.96(−) | 1.25 | 0.63 | 4.34(−) | 1.56 | 1.47 |
| Hex:IPA:CHCl₃ 85:5:10 | 1.74(−) | 1.21 | 0.74 | 3.52(−) | 1.63 | 1.52 |
| Hex:IPA:CHCl₃ 75:5:20 | 1.02(−) | 1.17 | 0.62 | 1.94(−) | 1.86 | 2.00 |
| Hex:IPA:CHCl₃ 78:2:20 | 2.16(−) | 1.12 | | 11.40(−) | — | — (not eluted) |

| | Racemic Compound 9 | | | Racemic Compound 10 | | |
|---|---|---|---|---|---|---|
| | k1 | α | Rs | k1 | α | Rs |
| Hex:IPA 90:10 | 1.67(+) | 1.20 | | 1.59(+) | 1.25 | 0.67 |
| Hex:IPA:CHCl₃ 90:5:5 | 1.71(+) | 1.41 | 1.29 | 1.12(+) | 1.26 | 0.79 |
| Hex:IPA:CHCl₃ 85:5:10 | 1.18(+) | 1.18 | 0.54 | 0.75(+) | 1.28 | 0.82 |
| Hex:IPA:CHCl₃ 75:5:20 | 0.59(+) | 1.48 | 1.16 | 0.34(+) | 1.33 | |
| Hex:IPA:CHCl₃ 78:2:20 | 1.01(+) | 1.55 | 1.40 | 0.69(+) | 1.35 | |

TABLE 12-continued

Cellulose tris(4-biphenylylcarbamate)

78:2:20

TABLE 13

Amylose tris(4-styrylphenylcarbamate)

| | Racemic Compound 5 | | | Racemic Compound 6 | | |
|---|---|---|---|---|---|---|
| | k1 | α | Rs | k1 | α | Rs |
| Hex:IPA 90:10 | 4.06(+) | 1.20 | 0.95 | 0.83(+) | 1.19 | 0.83 |
| Hex:IPA:CHCl₃ 90:5:5 | 4.16(+) | 1.19 | 0.92 | 0.71(+) | 1.24 | 0.88 |
| Hex:IPA:CHCl₃ 85:5:10 | 2.77(+) | 1.20 | 1.09 | 0.51(+) | 1.25 | 0.76 |
| Hex:IPA:CHCl₃ 75:5:20 | 1.47(+) | 1.19 | 1.08 | 0.35(+) | 1.32 | 1.17 |
| Hex:IPA:CHCl₃ 78:2:20 | 1.65(+) | 1.19 | 1.07 | 0.36(+) | 1.31 | 0.67 |

| | Racemic Compound 7 | | | Racemic Compound 8 | | |
|---|---|---|---|---|---|---|
| | k1 | α | Rs | k1 | α | Rs |
| Hex:IPA 90:10 | 1.27(−) | 1.13 | | 1.31(+) | 2.53 | 1.26 |
| Hex:IPA:CHCl₃ 90:5:5 | 2.02(−) | 1.16 | 0.51 | 2.67(+) | 3.27 | 1.90 |
| Hex:IPA:CHCl₃ 85:5:10 | 1.72(−) | 1.17 | 0.62 | 2.19(+) | 3.29 | 2.28 |
| Hex:IPA:CHCl₃ 75:5:20 | 1.12(−) | 1.29 | 0.99 | 1.57(+) | 3.44 | 3.06 |
| Hex:IPA:CHCl₃ 78:2:20 | 2.32(−) | 1.24 | 0.82 | 5.12(+) | — (not eluted | |

| | Racemic Compound 9 | | | Racemic Compound 10 | | |
|---|---|---|---|---|---|---|
| | k1 | α | Rs | k1 | α | Rs |
| Hex:IPA 90:10 | 1.69(+) | 1.31 | 0.60 | 1.54(+) | 1.09 | |
| Hex:IPA:CHCl₃ 90:5:5 | 1.75(+) | 1.37 | 0.77 | 1.30(+) | 1.11 | |
| Hex:IPA:CHCl₃ 85:5:10 | 1.28(+) | 1.43 | 1.24 | 0.83(+) | 1.15 | |
| Hex:IPA:CHCl₃ 75:5:20 | 0.80(+) | 1.54 | 1.84 | 0.44(+) | 1.19 | |
| Hex:IPA:CHCl₃ 78:2:20 | 1.03(+) | 1.54 | 1.91 | 0.52(+) | 1.23 | 0.69 |

TABLE 14

Amylose tris(4-biphenylylcarbamate)

| | Racemic Compound 5 | | | Racemic Compound 6 | | |
|---|---|---|---|---|---|---|
| | k1 | α | Rs | k1 | α | Rs |
| Hex:IPA 90:10 | 4.97(+) | 1.23 | 1.42 | 0.78(+) | 1.30 | 1.00 |
| Hex:IPA:CHCl₃ 90:5:5 | 5.12(+) | 1.33 | 2.13 | 0.75(+) | 1.31 | 1.37 |
| Hex:IPA:CHCl₃ 85:5:10 | 3.30(+) | 1.30 | 2.05 | 0.53(+) | 1.33 | 1.28 |
| Hex:IPA:CHCl₃ 75:5:20 | 1.75(+) | 1.27 | 1.77 | 0.31(+) | 1.36 | 0.90 |
| Hex:IPA:CHCl₃ 78:2:20 | 2.70(+) | 1.29 | 2.05 | 0.41(+) | 1.43 | 1.30 |

| | Racemic Compound 7 | | | Racemic Compound 8 | | |
|---|---|---|---|---|---|---|
| | k1 | α | Rs | k1 | α | Rs |
| Hex:IPA 90:10 | 1.63(−) | 1.35 | 0.93 | 1.46(+) | 2.48 | 1.84 |
| Hex:IPA:CHCl₃ 90:5:5 | 2.54(−) | 1.31 | 0.99 | 3.03(+) | 2.97 | 2.15 |
| Hex:IPA:CHCl₃ 85:5:10 | 2.17(−) | 1.31 | 1.15 | 2.63(+) | 3.31 | 2.44 |
| Hex:IPA:CHCl₃ 75:5:20 | 1.33(−) | 1.31 | 1.01 | 1.92(+) | 4.11 | 2.50 |
| Hex:IPA:CHCl₃ 78:2:20 | 2.72(−) | 1.29 | 0.97 | 8.99(+) | — | — (not eluted) |

| | Racemic Compound 9 | Racemic Compound 10 |
|---|---|---|

TABLE 14-continued

| Amylose tris(4-biphenylylcarbamate) | | | | | |
|---|---|---|---|---|---|
| | k1 | α | Rs | k1 | α | Rs |
| Hex:IPA 90:10 | 2.21(+) | 1.49 | 1.50 | 1.78(+) | 1.12 | |
| Hex:IPA:CHCl₃ 90:5:5 | 2.32(+) | 1.49 | 1.49 | 1.38(+) | 1.15 | 0.66 |
| Hex:IPA:CHCl₃ 85:5:10 | 1.60(+) | 1.50 | 1.73 | 0.89(+) | 1.17 | 0.63 |
| Hex:IPA:CHCl₃ 75:5:20 | 0.78(+) | 1.55 | 1.80 | 0.47(+) | 1.20 | |
| Hex:IPA:CHCl₃ 78:2:20 | 1.14(+) | 1.54 | 2.02 | 2.21(+) | 1.16 | 1.18 |

As the relative amount of chloroform to the cellulose tris(4-styrylphenylcarbamate) or tris(4-biphenylylcarbamate) increased, the elution time shortened. Although the α values thereof for the racemic compounds (8), (9) and (10) were improved, those for (5) and (6) scarcely changed and that for the compound (7) was reduced.

When amylose tris(4-styrylphenylcarbamate) was used, the α values for the racemic compounds (6), (7), (8), (9) and (10) were increased. When amylose tris(4-biphenylylcarbamate) was used, the α values for the racemic compounds (6), (8), (9) and (10) were increased. Particularly, the α value was considerably increased when a combination of racemic compound (8) with amylose tris(4-styrylphenylcarbamate or tris (4-biphenylylcarbamate) was used.

When hexane/2-propanol/chloroform (78:2:20) was used as the eluent, the elution time for racemic compound (8) was quite long and only one enantiomer was eluted even after 100 min with cellulose tris(4-biphenylylcarbamate), amylose tris(4-styrylphenylcarbamate) or amylose tris(4-biphenylylcarbamate).

For comparison, the results of the resolution obtained by using amylose triphenylcarbamate as the packing material and varying the proportion of the components of the eluent are shown in Table 15. As the relative amount of chloroform was increased, the elution time was reduced. Though a slight increase in the A value was observed for racemic compound (8), the values for other racemic compounds were substantially unchanged.

TABLE 15

| | Amylose triphenylcarbamate | | | | | | | |
|---|---|---|---|---|---|---|---|---|
| | Hex:IPA (90:10) | | Hex:IPA:CHCl₃ (90:5:5) | | Hex:IPA:CHCl₃ (85:5:10) | | Hex:IPA:CHCl₃ (75:5:20) | |
| Racemic Compounds | k1 | α | k1 | α | k1 | α | k1 | α |
| 5 Ph-CH(OH)-C(=O)-Ph | 3.72(+) | ~1 | 4.21(+) | ~1 | 2.91(+) | ~1 | 1.60(+) | ~1 |
| 6 binaphthol-dimethyl structure | 1.15(−) | 1.53 | 2.04(−) | 1.52 | 1.69(−) | 1.55 | 1.14(−) | 1.55 |
| 8 cyclopropane-1,2-di(CONHPh) | 1.83(+) | 1.52 | 4.60(+) | 1.43 | 3.92(+) | 1.60 | 3.12(+1) | 1.76 |
| 9 Ph—CH(OH)—Tr | 1.51(+) | 1.84 | 1.61(+) | 1.84 | 1.16(+) | 1.85 | 0.67(+) | 1.85 |
| 10 N,N-heterocycle | 0.77(+) | 1.28 | 0.84(+) | 1.30 | 0.58(+) | 1.32 | 0.33(+) | 1.31 |

In Table 16, differences between the α value of the packing material obtained when hexane/2-propanol/chloroform (75:5:20) was used as the eluent and that obtained when hexane/2-propanol (90:10) was used are shown in parentheses. For comparison, the α values of cellulose and amylose tris(3,5-dimethylphenylcarbamates) having a high optical resolution capacity are also shown. When the racemic compound (8) and amylose tris(4-biphenylylcarbamate) were used, the α value was the highest, i.e., 4.11. When the racemic compound (9) and amylose tris(4-biphenylylcarbamate were used, the value was 1.55 and when the racemic compound (10) and cellulose tris(4-biphenylylcarbamate) were used, the α value was 1.33, which were far higher than those obtained when cellulose and amylose tris(3,5-dimethylphenylcarbamate) were used.

TABLE 16

Separation factors (α) on cellulose and amylose triphenylcarbamate derivatives
(General formula for cellulose and amylose derivatives in Table 10)

| Racemic Compounds | X = | Cellulose derivatives | | | | Amylose derivatives | | | |
|---|---|---|---|---|---|---|---|---|---|
| | | —CH=CH—[a] 1 | [a] (phenyl) 2 | 3,5-(CH$_3$)$_2$[b] | 3 (phenyl) | —CH=CH—[a] 3 | [a] (phenyl) 4 | 3,5-(CH$_3$)$_2$[b] |
| 5 (Ph-CH(OH)-CH=O, Ph) | | ~1 (−0.05) | ~1 (0.00) | 1.58 | 1.19 (−0.01) | 1.27 (+0.04) | 1.21 |
| 6 (bicyclohexyl diol/dimethyl) | | 1.20 (−0.11) | 1.17 (−0.18) | 1.83 | 1.29 (+0.16) | 1.31 (−0.04) | 2.11 |
| 8 (cyclopropane bis-CONHPh) | | 1.22 (+0.22) | 1.86 (+0.55) | 3.17 | 3.44 (+0.91) | 4.11 (+1.63) | 2.01 |
| 9 Ph—CH—OH, Tr | | 1.19 (+0.19) | 1.48 (+0.28) | 1.34 | 1.54 (+0.23) | 1.55 (+0.06) | 1.98 |
| 10 (bis-benzyl diamine) | | 1.25 (0.06) | 1.33 (+0.08) | 1.32 | 1.19 (+0.10) | 1.20 (+0.08) | 1.58 |

[a], Eluent, Hex:IPA:CHCl$_3$ (75:5:20)
[b], Eluent, Hex:IPA (90:10)

EXAMPLE 15

3 grams of silica gel (RA-227-1) having a particle diameter of 7 μm and a pore diameter of 10 Å which had been surface-treated with 3-aminopropyltriethoxysilane was uniformly moistened five times with a solution of 0.75 g of cellulose tris(2-phenylethynylphenylcarbamate) in 20-ml of THF, the solution being divided into five portions and each portion being used each time. The product was sufficiently dried in a vacuum line in an evaporator. After the particle size classification with hexane/2-propanol, the product was packed in a stainless steel column having a length of 25 cm and an inner diameter of 0.46 cm by the slurry packing method. The number of theoretical stages was 2400 and the dead time was 6.08 min.

A solution of cellulose tris[4-(2-phenylethynyl)phenylcarbamate] in THF was cast on a slide glass plate and observed with a polarizing microscope to reveal that it was crystalline. 0.305 mg/μl solution of cellulose tris[4-(2-phenylethynyl)phenylcarbamate] in THF was prepared and the liquid-crystal property thereof was examined. The solution was green, since cellulose tris[4-(2-phenylethynyl)phenylcarbamate] per se was a green polymer. After a few days, the solution was slightly pearly.

Though the exact σ-value of

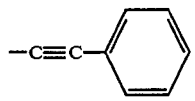

was unknown, it was supposedly a weakly electron-attractive group, since acetone elution time thereof was 10.97 min.

It was supposed that when chloroform was added to the eluent, chloroform surrounded the phenyl group owing to the interaction between chloroform and the phenyl group to change the resolution power. Therefore, hexane/2-propanol/chloroform (90:5:5) was used as the eluent. As a result, the resolution power was higher than that of hexane/2-propanol (90:10), though the extent of the increase varied depending on the compounds such as

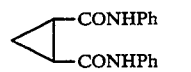

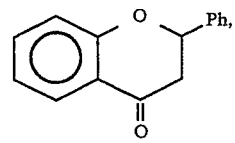

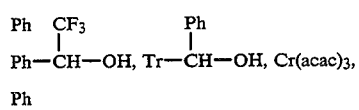

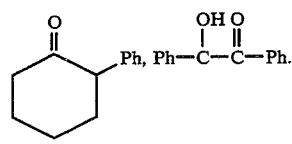

On the contrary, the resolution power for

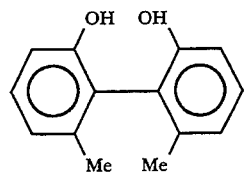

and Tröger base was reduced (see Table 17).

TABLE 17

The results of optical resolution with cellulose tris[4-(2-phenylethynyl)phenylcarbamate] at 25° C.

| Racemate | Hex:IPA 90:10 | | | Hex:IPA:CHCl₃ 90:5:5 | | |
|---|---|---|---|---|---|---|
| | k' | α | Rs | k' | α | Rs |
| (binaphthol with OH, OH, Me, Me) | 1.31(−) | 1.27 | 0.68 | 2.21 | 1.14 | |
| (cyclopropane with CONHPh, CONHPh) | 2.46(−) | 1.46 | | 5.48 | 1.57 | 1.66 |
| (cyclopropane with CONHPh, Ph) | 4.17(−) | 1.94 | 2.60 | | | |
| Tröger base | 2.11(+) | 1.13 | 0.72 | 1.01 | 1.07 | |

TABLE 17-continued

The results of optical resolution with cellulose tris[4-(2-phenylethynyl)phenylcarbamate] at 25° C.

| Racemate | Hex:IPA 90:10 | | | Hex:IPA:CHCl$_3$ 90:5:5 | | |
|---|---|---|---|---|---|---|
| | k' | α | Rs | k' | α | Rs |
| (chromanone with Ph) | 3.33(−) | 1.09 | | 3.23 | 1.10 | 1.02 |
| (aziridine Ph, Ph) | 0.84(+) | 1.68 | 2.83 | 0.73 | 2.00 | 3.89 |
| Ph—CHOH with CF$_3$, Ph, Ph | 1.18(−) | 1.20 | 0.75 | 1.99 | 1.30 | 1.95 |
| Tr—CH—OH, Ph | 2.25(+) | 1.50 | 2.58 | 1.28 | 1.69 | 2.55 |
| Co(acac)$_3$ | 7.82(+) | 1.41 | 2.29 | | | |
| Cr(acac)$_3$ | 5.82(−) | 1.54 | 1.95 | 2.52 | 1.56 | 1.94 |
| (cyclohexanone-Ph) | 2.75(−) | 1.14 | 0.79 | 1.35 | 1.16 | 1.02 |
| (benzoin / Ph-C(O)-C(OH)-Ph) | 6.29(−) | 1.25 | 2.57 | 6.99 | 1.27 | 2.63 |
| (spiroindanedione) | 10.02(+) | 1.02 | | 4.16 | 1.04 | |

EXAMPLE 16

Silica gel (RA 227-1) having a particle diameter of 7 μm and a pore diameter of 4000 Å which had been surface-treated with 3-aminopropyltriethoxysilane was used. 0.75 grams of cellulose tris(4-phenoxyphenylcarbamate) was dissolved in 10 ml of THF. 3.02 grams of the surface-treated silica gel (RA 227-1) was uniformly moistened with about 2.5 ml of THF Solution and then sufficiently dried in a vacuum line in an evaporator. This procedure was repeated four times. 0.76 g of amylose tris(4-phenoxyphenylcarbamate) was dissolved in 10 ml of THF. The same treatment as that of cellulose tris(4-phenoxyphenylcarbamate) was conducted except that 3.02 grams of RA 227-1 was used.

The packing material prepared in the above step was subjected to particle size classification with hexane/2-propanol and packed in a stainless steel column having a length of 25 cm and an inner diameter of 0.46 cm by the slurry packing method.

When 0.5 ml/min of hexane/2-propanol (90:10) (25° C.) was used as the eluent, the number of theoretical plates for benzene was 2700 [cellulose tris(4phenoxyphenylcarbamate)] and 3000 [amylose tris(4-phenoxyphenylcarbamate)].

Cellulose tris( 4-phenoxyphenylcarbamate ) formed liquid crystals in THF. The high crystallinity of this compound was confirmed by casting on a glass plate followed by observation with a polarizing microscope. Amylose carbamate was also cast from THF and observed with a polarizing microscope to reveal that it formed no liquid crystals, though it formed crystals.

Since both compounds were highly soluble in chloroform, hexane/2-propanol (90:10) free from chloroform was used as the eluent.

In the results of the resolution obtained with cellulose tris(4-phenoxyphenylcarbamate), the resolution result far racemic compound 13 was better (α=1.53) than those obtained with cellulose tris(3,5 dimethylphenylcarbamate) and cellulose tris(3,5 dichlorophenylcarbamate) and α values for racemic compounds 15 and 16 were as high as 1.81 and 1.72, respectively. It is apparent from Table 18 that the α values for racemic compounds 16, 17 and

were quite as high as 1.72, 3.04 and 1.32, respectively. Thus, high resolution capacities were obtained when the anilide compounds were used. The α values, for

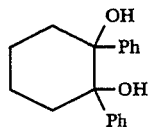

was 1.29.

In the results of the resolution obtained with amylose tris(4-phenoxyphenylcarbamate), the racemic compounds which could not be resolved with amylose tris(3,5 dimethylphenylcarbamate) and amylose tris(3,-5dichlorophenylcarbamate) could be resolved with amylose tris(4-phenoxyphenylcarbamate), though the α values were low (α=1.08 and 1.16, respectively). In the results of the resolution of racemic compounds 8 and 13, excellent resolution results (α=2.24) and 2.12) were obtained.

TABLE 18

| The results of resolution with 1 and 4 | | | | | | |
|---|---|---|---|---|---|---|
| | Cellulose tris(4-phenoxyphenylcarbamate) | | | Amylose tris(4-phenoxyphenylcarbamate) | | |
| Racemate | $k_1'$ | α | Rs | $k_1'$ | α | Rs |
| 2,2'-dihydroxy-6,6'-dimethylbiphenyl  7 | 1.44(−) | 1.15 | | 1.21(−) | 1.55 | 1.31 |
| 1,3-diphenylacetone  8 | 0.82(+) | 1.37 | 1.70 | 0.74(+) | 2.24 | 3.75 |
| Ph—C(OH)—C(O)—Ph  9 | 4.78(−) | 1.10 | 0.77 | 5.51(+) | 1.19 | 1.40 |
| Tröger base  10 | 1.75(−) | −1 | | 1.42(+) | 1.55 | 1.75 |
| flavanone  11 | 3.07(−) | 1.15 | 1.46 | 2.76(?) | 1.04 | |
| Ph—CH(CF_3)(OH)—Ph  12 | 1.00(−) | 1.33 | 1.31 | 0.85(+) | 1.11 | |
| Tr—CH(Ph)—OH  13 | 1.92(+) | 1.53 | 1.61 | 2.39(+) | 2.12 | 2.24 |
| 2-phenylcyclohexanone  14 | 1.94(−) | 1.12 | 0.67 | 1.66(+) | 1.08 | |
| Co(acac)_3  15 | 1.68(+) | 1.81 | 1.72 | 1.66(+) | 1.16 | |
| cyclopropane-1,2-di(CONHPh)  16 | 2.14(−) | 1.72 | 1.21 | 1.49(+) | 1.32 | |
| cyclopropane-CONHPh, Ph  17 | 4.03(−) | 3.04 | 3.16 | 2.90(+) | 1.70 | |
| Cr(acac)_3  18 | 2.08(+) | 2.27 | 3.31 | 1.41(+) | 1.15 | |

TABLE 18-continued

| | The results of resolution with 1 and 4 | | | | | |
|---|---|---|---|---|---|---|
| | Cellulose tris(4-phenoxyphenylcarbamate) | | | Amylose tris(4-phenoxyphenylcarbamate) | | |
| Racemate | $k_1'$ | α | Rs | $k_1'$ | α | Rs |
| 19 | 1.11(−) | 1.15 | | 1.14(−) | 1.09 | |
| 20 | 1.55(−) | ~1 | | 1.18(+) | ~1 | |

TABLE 19

| | The results of resolution with cellulose derivatives | | | | | | | | |
|---|---|---|---|---|---|---|---|---|---|
| | tris(4-phenoxy phenylcarbamate) | | | tris(3,5 dimethyl phenylcarbamate) | | | tris(3,5 dichloro- phenylcarbamate) | | |
| Racemate | k1 | α | $R_s$ | k1 | α | $R_s$ | k1 | α | $R_s$ |
| 7 | 1.44(−) | 1.15 | | 2.36(−) | 1.83 | 4.39 | 1.62(+) | 1.11 | 0.75 |
| 8 | 0.82(+) | 1.37 | 1.70 | 0.74(−) | 1.68 | 3.22 | 0.56(+) | 1.84 | 4.20 |
| 9 | 4.78(−) | 1.10 | 0.77 | 2.43(+) | 1.58 | 4.38 | 3.08(−) | 1.21 | 1.91 |
| 10 | 1.75(−) | ~1 | | 0.98(+) | 1.32 | 1.92 | 0.87(+) | 1.65 | 3.89 |
| 11 | 3.07(−) | 1.15 | 1.46 | 1.47(−) | 1.41 | 3.08 | 1.55(−) | 1.20 | 1.48 |
| 12 | 1.00(−) | 1.33 | 1.31 | 2.13(−) | 2.59 | 6.40 | 0.28(−) | 1.38 | 0.87 |
| 13 | 1.92(+) | 1.53 | 1.61 | 1.37(+) | 1.34 | 1.87 | 0.40(+) | 1.29 | 0.84 |
| 14 | 1.94(−) | 1.12 | 0.67 | 1.17(−) | 1.15 | 0.90 | 2.65(−) | 1.26 | 1.95 |
| 15 | 1.68(+) | 1.81 | 1.72 | 0.42(+) | ~1 | | 0.76(+) | 1.82 | 4.06 |
| 16 | 2.14(−) | 1.72 | 1.21 | 0.83(+) | 3.17 | 6.17 | 0.59(+) | 1.41 | 1.47 |

TABLE 20

| | The results of resolution with amylose derivatives | | | | | | | | |
|---|---|---|---|---|---|---|---|---|---|
| | tris(4-phenoxy phenylcarbamate) | | | tris(3,5 dimethyl phenylcarbamate) | | | tris(3,5 dichloro- phenylcarbamate) | | |
| Racemate | k1 | α | $R_s$ | k1 | α | $R_s$ | k1 | α | $R_s$ |
| 7 | 1.21(−) | 1.55 | 1.31 | 2.46(−) | 2.11 | 6.38 | 1.10(+) | ~1 | |
| 8 | 0.74(+) | 2.24 | 3.75 | 0.42(+) | 3.04 | 6.67 | 0.50(+) | 1.32 | 1.69 |
| 9 | 5.51(+) | 1.19 | 1.40 | 3.14(−) | 1.21 | 2.07 | 6.08(+) | ~1 | |
| 10 | 1.42(+) | 1.55 | 1.75 | 0.53(+) | 1.58 | 2.30 | 0.85(+) | 1.34 | 2.27 |
| 11 | 2.76(?) | 1.04 | | 0.93(+) | 1.12 | 0.77 | 1.62(+) | 1.10 | 1.02 |
| 12 | 0.85(+) | 1.11 | | 1.30(+) | 1.15 | 0.75 | 0.37 | 1.00 | |
| 13 | 2.39(+) | 2.12 | 2.24 | 2.65(+) | 1.98 | 5.48 | 0.88(+) | 2.25 | 6.05 |
| 14 | 1.66(+) | 1.08 | | 0.61(−) | ~1 | | 1.26(−) | ~1 | |
| 15 | 1.66(−) | 1.16 | | 0.25(−) | ~1 | | 0.63(+) | ~1 | |
| 16 | 1.19(+) | 1.32 | | 3.25(+) | 2.01 | 3.59 | 0.59(−) | 1.11 | |

The embodiments of the invention in which an exclusive property or privilege is claimed are defined as follows:

1. A method of separating a chemical substance from a mixture containing the same, which comprises the step of treating said mixture with a polysaccharide derivative selected from the group consisting of cellulose tris (4-styrylphenyl) and cellulose tris-3-(2-thienyl) acrylate.

2. A method as claimed in claim 1, in which said mixture is a mixture of optical isomers.

3. A method as claimed in claim 1, in which the method is conducted through a chromatographic column or layer.

4. A method as claimed in claim 1, wherein said polysaccharide derivative is supported on a porous particulate carrier in an amount of from 1–100 wt. % based on said carrier.

5. A method as claimed in claim 4, wherein said carrier is from 1–300 μm in size.

6. A method as claimed in claim 4, wherein the pore size of said carrier is from 50–50,000 Å.

7. A method as claimed in claim 1, wherein said derivative is supported on a porous particulate carrier in an amount preferably from 5–50 wt. % based on said carrier.

8. A method effective for separating chemical substances from mixtures thereof and for separating optical isomers from mixtures thereof, which comprises the step of contacting said mixture, under conditions effective for chromatographic separation, with a chromatographic separating agent comprising a derivative of a polysaccharide selected from the group consisting of cellulose tris (4-styrylphenyl) and cellulose tris-3-(2-thienyl) acrylate.

9. The method of claim 8, wherein the chromatographic separating agent is supported on silica beads.

* * * * *